(12) United States Patent
Ruddock

(10) Patent No.: US 9,976,164 B2
(45) Date of Patent: May 22, 2018

(54) METHOD FOR PRODUCING NATIVELY FOLDED PROTEINS IN A PROKARYOTIC HOST

(71) Applicant: University of Oulu, Oulu (FI)

(72) Inventor: Lloyd Ruddock, Oulu (FI)

(73) Assignee: University of Oulu, Oulu (FI)

( * ) Notice: Subject to any disclaimer, the term of this patent is extended or adjusted under 35 U.S.C. 154(b) by 0 days. days.

(21) Appl. No.: 14/963,775

(22) Filed: Dec. 9, 2015

(65) Prior Publication Data

US 2016/0090615 A1 Mar. 31, 2016

Related U.S. Application Data

(63) Continuation of application No. 13/309,722, filed on Dec. 2, 2011, now Pat. No. 9,238,817, which is a continuation-in-part of application No. PCT/FI2010/050448, filed on Jun. 2, 2010.

(30) Foreign Application Priority Data

Jun. 2, 2009 (FI) ..................................... 20095615

(51) Int. Cl.
| | |
|---|---|
| *C12P 21/06* | (2006.01) |
| *C12P 21/00* | (2006.01) |
| *C12N 9/02* | (2006.01) |
| *C12N 9/90* | (2006.01) |
| *C12N 15/70* | (2006.01) |
| *C12P 21/02* | (2006.01) |
| *C07K 14/47* | (2006.01) |
| *C07K 14/51* | (2006.01) |
| *C07K 14/53* | (2006.01) |
| *C07K 14/54* | (2006.01) |
| *C07K 14/555* | (2006.01) |
| *C07K 14/575* | (2006.01) |
| *C07K 14/61* | (2006.01) |
| *C07K 14/705* | (2006.01) |

(52) U.S. Cl.
CPC .......... *C12P 21/00* (2013.01); *C07K 14/4703* (2013.01); *C07K 14/51* (2013.01); *C07K 14/53* (2013.01); *C07K 14/54* (2013.01); *C07K 14/5412* (2013.01); *C07K 14/555* (2013.01); *C07K 14/575* (2013.01); *C07K 14/61* (2013.01); *C07K 14/70596* (2013.01); *C12N 9/0051* (2013.01); *C12N 9/90* (2013.01); *C12N 15/70* (2013.01); *C12P 21/02* (2013.01); *C12Y 108/03002* (2013.01); *C12Y 503/04001* (2013.01)

(58) Field of Classification Search
None
See application file for complete search history.

(56) References Cited

U.S. PATENT DOCUMENTS

| | | | | |
|---|---|---|---|---|
| 5,529,926 A | * | 6/1996 | Maat ...................... | A21D 8/042 435/189 |
| 6,027,888 A | * | 2/2000 | Georgiou ........... | C07K 14/8117 435/243 |
| 6,361,964 B1 | * | 3/2002 | Kaiser .................. | C07K 1/1133 435/233 |
| 2007/0193977 A1 | | 8/2007 | Lee et al. | |

FOREIGN PATENT DOCUMENTS

| | | |
|---|---|---|
| KR | 20070041166 A | 4/2007 |
| WO | 2005061718 A1 | 7/2005 |
| WO | 2009058956 A1 | 5/2009 |
| WO | WO 2009/058956 * | 5/2009 |

OTHER PUBLICATIONS

Gerber et al., J. Biol. Chem., 276, 26, 23486-23491, 2001.*
Senkovich, Proc. Nat. Acad. Sci, USA, 97, 22:12068-12073, 2000.*
Wang et all., Biochemistry 46:3246-3254, 2007.*
Lisowsky et al., Digest Liver Dis., 33:173-180, 2001.*
Kadokura et al., Nat. Cell Biol., 3: E247-249, 2001.*
Novagen, User Protocol TB009, Rev. F0104, 2004.*
FI20095615 Search report, Patentti—ja rekisterihallitus, dated Jan. 29, 2010.

* cited by examiner

*Primary Examiner* — Nancy A Treptow
(74) *Attorney, Agent, or Firm* — Berggren LLP

(57) ABSTRACT

The present invention relates to a method for producing a protein of interest containing one or more disulfide bonds in its native state. The method comprises that a prokaryotic host cell is genetically engineered to express the protein of interest and a sulfhydryl oxidase in the cytoplasm of the host cell. The protein of interest is formed in a soluble form and contains disulfide bonds due to the presence of the sulfhydryl oxidase in the cytoplasm of said host cell. The present invention relates also to a prokaryotic host cell and a vector system for producing a protein of interest containing natively folded disulfide bonds.

13 Claims, 15 Drawing Sheets

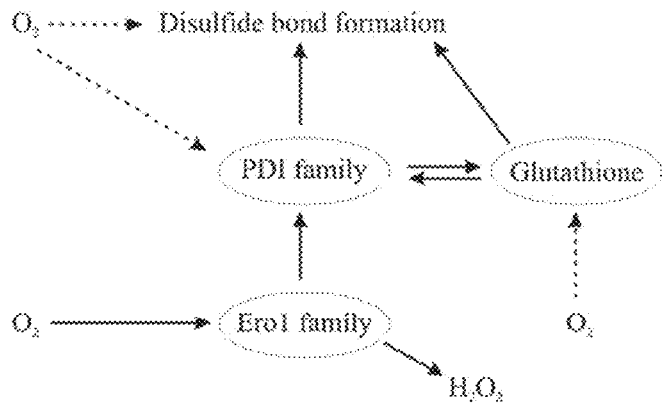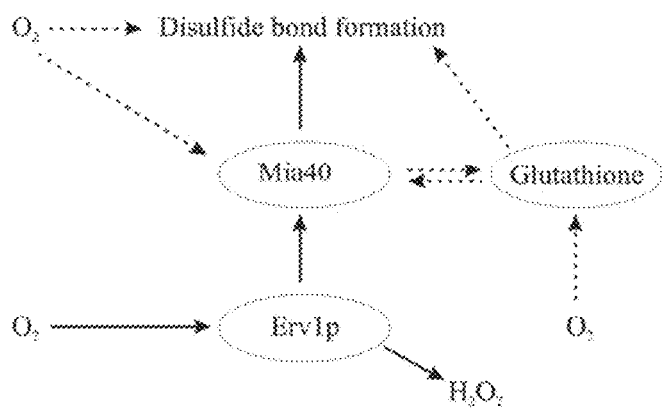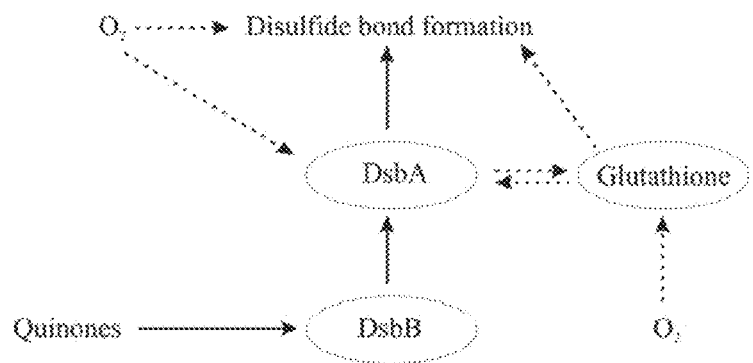
Fig. 1

Endoplasmic oxidoreductin-1 from *Saccharomyces cerevisiae* (Swiss-Prot ID Q03103) (SEQ ID NO:1):

MRLRTAIATLCLTAFTSATSNNSYIATDQTQNAFNDTHFCKVDFNDHVSPSCNVTFNELNAINENIRDDLSALLKSDFFK
YFRLDLYKQCSFWDANDGLCLNPACSVDVVEDWDTLPEYWQPEILGSFMNDTMKEADDSDDECKFLDQLCQTSKKPVDIE
DTINYCDVNDFNGKNAVLIDLTANPERFTGYGGKQAGQIWSTIYQDNCFTIGETGESLAKDAFYRLVSGFHASIGTHLSK
EYLNTKTGKWEPNLDLFMARIGNFPDRVTNMYFNYAVVAKALWKIQPYLPEFSFCDLVNKEIKNKMDNVISQLDTKIFNE
DLVFANDLSLTLKDEFRSRFKNVTKIMDCVQCDRCRLWGKIQTTGYATALKILFEINDADEPTKQHIVGKLTKYELIALL
QTFGRLSESIESVNMFEKMYGKRLNGSENRLSSFFQNNFFNILKEAGKSIRYTIENINSTKEGKKKTNNSQSHVFDDLKM
PKAEIVPRFSNGTVNKWKKAWNTEVNNVLEAFRFIYRSYLDLPRNIWELSLMKVYKFWNKFIGVADYVSEETREPISYKL
DIQ

Human ERO1-like protein alpha (Swiss-Prot ID Q96HE7) (SEQ ID NO:2):

MGRGWGFLFGLLGAVWLLSSGHGEEQPPETAAQRCFCQVSGYLDDCTCDVETIDRFNNYRLFPRLQKLLESDYFRYYKVN
LKRPCPFWNDISQCGRRDCAVKPCQSDEVPDGIKSASYKYSEEAANNLIEECEQAERLGAVDESLSEETQKAVLQWTKHDD
SSDNFCEADDIQSPEAEYVDLLLNPERYTGYKGPDAWKIWNVIYEENCFKPQTIKRPLNPLASGQGTSEENTFYSWLEGL
CVEKRAFYRLISGLHASINVHLSARYLLQETWLEKKWGHNITEFQQRFDGILTEGEGPRRLKNLYFLYLIELRALSKVLP
FFERPDFQLFTGNKIQDEENKMLLLEILHEIKSPPLHFDENSFFAGDKKEAHKLKEDFRLHFRNISRIMDCVGCFKCRLW
GKLQTQGLGTALKILFSEKLIANMPESGPSYEFHLTRQEIVSLFNAFGRISTSVKELENFRNLLQNIH

Human ERO1-like protein beta (Swiss-Prot ID Q86YB8) (SEQ ID NO:3):

MSQGVRRAGAGQGVAAAVQLLVTLSFLRSVVEAQVTGVLDDCLCDIDSIDNFNTYKIFPKIKKLQERDYFRYYKVNLKRP
CPFWAEDGHCSIKDCRVEPCPESKIPVGIKACHSNKYLFMANNTKELEDCEQANKLCAINSTLSNQSKEAFIDWARYDDS
RDHFCELDDERSPAAQYVDLLLNPERYTGYKGTSAWRVWNSIYEENCFKPRSVYRPLNPLAPSRGEDDGESFYTWLEGLC
LEKRVFYKLISGLHASINLHLCANYLLEETWGKFSWGPNIKEFKHRFDPVETKGEGPRRLKNLYFLYLIELPALSKVAPY
FERSIVDLYTGNAEEDADTKTLLLNIFQDTKSFPMHFDEKSMFAGDKKGAKSLKEEFRLHFKNISRIMDCVGCDKCRLWG
KLQTQGLGTALKILFSEKEIQKLPENSPSKGFQLTRQEIVALLNAFGRLSTSIRDLQKFKVLLQHSR

Fig. 3

Human ALR (Swiss-Prot ID P55789) (SEQ ID NO:4):

MAAPGERGRFHGGNLFFLPGGARSEMMDDLATDARGRGAGRRQAAASASTPAQAPTSDSPVAEDASRRRPCRACVDFKTW
MRTQQKRDTKFREDCPPDREELGRHSWAVLHTLAAYYPDLPTPEQQQDMAQFIHLFSKFYPCEECAEDLRKRLCRNHPDT
RTRACFTQWLCHLHNEVNRKLGKPDFDCSKVDERWRDGWKDGSCD

S. cerevisiae mitochondrial FAD-linked sulfhydryl oxidase ERV1 (Swiss-Prot ID P27882) (SEQ ID NO:5):

MKAIDKMTDNPPQEGLSGRKIIYDEDGKPCRSCNTLLDFQYVTGKISNGLFNLSSNGKLAGTGALTGEASELMPGSRTYR
KVDPPDVEQLGRSSWTLLHSVAASYPAQPTDQQKGEMKQFLNIFSHIYPCNWCAKDPEKYIRENAPQVESREELGRWMCE
AHNKVNKKLRKPKFDCNFWEKRWKDGWDE

S. cerevisiae FAD-linked sulfhydryl oxidase ERV2 (Swiss-Prot ID Q12284) (SEQ ID NO:6).

MKQIVKRSHAIRIVAALGIIGLWMFFSSNELSIATFGLIKAKSGIDEVQGAAAEKNDARLKEIEKQTIMPLMGDDKVKKE
VGRASWKYFHTLLARFPDEPTPEEREKLHTFIGLYAELYPCGECSYHPVKLIEKYPVQTSSPTAAAMWGCHIHNKVNEYL
KKDIYDCATILEDYDCGCSDSDGKRVSLEKEAKQHG

Human sulfhydryl oxidase 1 (QSOX; Swiss-Prot ID O00391) (SEQ ID NO:7):

MRRCNSGSGPPPSLLLLLLWLLAVPGANAAPRSALYSPSDPLTLLQADTVRGAVLGSRSAWAVEFFASWCGHCIAFAPTW
KALAEDVKAWRPALYLAALDCAEETNSAVCRDFNIPGFPTVRFFKAPTKNGSGAVFPVAGADVQTLRERLIDALESHHDT
WPPACPPLEPAKLEEIDGFFARNNEEYLALIFEKGGSYLGREVALDLSQHKGVAVRRVLNTEANVRKFGVTDFPSCYLL
FRNGSVSRVPVLMESRSFYTAYLQRLSGLTREAAQTTVAPTTANKIAPTVWKLADRSKIYMADLESALHYILRIEVGRFP
VLEGQRLVALKKFVAVLAKYFPGRPLVQNFLHSVNEWLKRQKRNKIPYSFFKTALDDRKEGAVLAKKVNWIGCQGSEPHF
RGFPCSLWVLFHFLTVQAARQNVDHSQEAAKAKEVLPAIRGYVHYFFGCRDCASHFEQMAAASMHRVGSPNAAVLWLWSS
HNRVNARLAGAPSEDPQFPKVQWPPRELCSACHNERLDVPVWDVEATLNFLKAHFSPSNIILDFPAAGSAARRDVQNVAA
APELAMGALELESRNSTLDPGKPEMMKSPTNTTPHVPAEGPEASRPPKLHPGLRAAPGQEPPEHMAELQRNEQEQPLGQW
HLSKRDFGAALLAESRAEKNRLWGPLEVRRVGRSSKQLVDIPEGQLEARAGRCRGQWLQVLGGGFSYLDISLCVGLYSLS
PMGLLAMYTYFQAKIRALKGHAGHPAA

Fig. 4A

Human sulfhydryl oxidase 2 (Swiss-Prot ID Q6ZRP7) (SEQ ID NO:8):

MAAAGAAVAPSPGIGAGPALRARRSPSPRAARLPPLLVLLAAAAVGPCAGGAARLXRAGEDAVWVLDSGSVRGATANSSA
AWLVQFYSSWCGHCIGYAPTWRALAGDVRDWASAIRVAALDCMEEKNQAVCHDYDIBFYPTFRYFKAPTKEFTTGENFKG
PDRELPTVRQIMIDFLQMHTEGSRPPACPRLDPIQPSDVLSLLDNRGSHYVAIVFESNSSYLGREVILDLIPYESIVVTR
ALDGDKAFLEKLGVSSVPSCYLIYPNGSHGLINVVKPLRAFFSSYLKSLPDVPKKSLPLPEKPHKEENSEIVVWREFDKS
KLYTVDLESGLHYLLRVELAAHKSLAGAELKTLKDFVTVLAKLFPGRPPVKKLLEMLQEWLASLPLDRIPYNAVLDLVNN
KMRISGIPLTNHIKWVGCQGSRSELRGYPCSLWKLFHTLTVEASTHPDALVGTGFESDPQAVLQTMPRYVHTFFGCKECG
EHFEEMAKESMDSVKTPDQAILWLWKKHNMVNGRLAGHLSEDPRFPKLQWPTPDLCPACHEEIKGLASWDEGHVLTFLKQ
HYGRDNLLDTYSADQGDSSEGGTLARGEEEEKRLTPPEVSHGDRDTQSVRPPGALGPRPALPESLHHSLDGKLQSLDGPG
AHKEVGGAAPFLGVDFSSLDMSLCVVLYVASSLFLMVMYFFRVRSRRWKVKHHHPAV

Vaccinia virus FAD-linked sulfhydryl oxidase E10 (Swiss-Prot ID P21050) (SEQ ID NO:9):

MNPKHWGRAVWTIIFIVLSQAGLDGNIEACKRKLYTIVSTLPCPACRRHATIAIEDNNVMSSDDLNYIYYFFIRLFNNLA
SDPKYAIDVSKVKPL

E.coli (K12 strain) DsbC (SEQ ID NO:10):

MKKGFMLFTLLAAFSGFAQADDAAIQQTLAKMGIKSSDIQPAPVAGMKTVLTNSGVLYITDDGKHIIQGPMYDVSGTAP
VNVTNKMLLKQLNALEKEMIVYKAPQEKHVITVFTDITCGYCHKLHEQMADYNALGITVRYLAFPROGLDSDAEKEMK
AIWCAKDKNKAFDDVMAGKSVAPASCDVDIADHYALGVQLGVSGTPAVVLSNGTLVPGYQPPKEMKEFLDEHQKMT
SGK

Human PDI (SEQ ID NO:11):

MLRRALLCLAVAALVRADAPEEEDHVLVLRKSNFAEALAAHKYLLVEFYAPWCGHCKALAPEYAKAAGKLKAEGSEIR
LAKVDATEESDLAQQYGVRGYPTIKFFRNGDTASPKEYTAGREADDIVNWLKKRTGPAATTLPDGAAAESLVESSEV
AVIGFFKDVESDSAKQFLQAAEAIDDIPFGITSNSDVFSKYQLDKDGVVLFKKFDEGRNNFEGEVTKENLLDFIKHNQL
PLVIEFTEQTAPKIFGGEIKTHILLFLPKSVSDYDGKLSNFKTAAESFKGKILFIFIDSDHTDNQRILEFFGLKKEECPAVRL
ITLEEEMTKYKPESEELTAERITEFCHRFLEGKIKPHLMSQELPEDWDKQPVKVLVGKNFEDVAFDEKKNVFVEFYAP
WCGHCKQLAPIWDKLGETYKDHENIVIAKMDSTANEVEAVKVHSFPTLKFFPASADRTVIDYNGERTLDGFKKFLESG
GQDGAGDDDDLEDLEEAEEPDMEEDDDQKAVKDEL

Fig. 4B

METHOD FOR PRODUCING NATIVELY FOLDED PROTEINS IN A PROKARYOTIC HOST

PRIORITY CLAIM

This is continuation patent application of U.S. patent application Ser. No. 13/309,722 filed Dec. 2, 2011, which is a continuation-in-part application of International application number PCT/FI2010/05448 filed on Jun. 2, 2010 claiming priority of the Finnish national patent application number 20095615 filed on Jun. 2, 2009, the contents of all of which are incorporated herein by reference in their entirety.

SEQUENCE DATA

This application contains sequence data provided in computer readable form and as PDF-format. The PDF-version of the sequence data is identical to the computer readable format.

FIELD OF THE INVENTION

This invention relates to a method, a host cell and a vector system for producing a protein of interest containing one or more disulfide bonds in its native state. In particular, the invention relates to a method, a host cell and a vector system for producing such proteins in a prokaryotic host.

DESCRIPTION OF RELATED ART

Many proteins and enzymes of biotechnological importance contain structure stabilizing disulfide bonds, with an estimated one third of all human proteins folding in the endoplasmic reticulum (ER) and acquiring disulfide bonds there. This includes most proteins which get secreted or end up on the outer membrane. Since any two cysteine residues in a protein have the potential to form a disulfide bond, the correct formation of native disulfide bonds is not trivial. Hence, it is unsurprising that native disulfide bond formation is often the rate-limiting step in the folding of proteins in vitro and in vivo.

The process of native disulfide bond formation in the endoplasmic reticulum (ER), periplasm or inter-membrane space of mitochondria is known to be catalysed by several families of enzymes. However, while some of the participants in the cellular process are known, their precise individual roles are still largely confused.

What is known is that native disulphide bond formation can occur via multiple parallel pathways (see FIG. 1). The current state of the art says that the major pathway for disulfide bond formation in the ER is via oxidation of protein disulfide isomerase (PDI) family members by the sulfhydryl oxidase activity of the gene product(s) of ERO1 family members. PDI in turn then introduces disulfide bonds into folding proteins.

Parallel pathways, for example via glutathione, are also possible. Similarly in the inter-membrane space of mitochondria a similar pathway exists via the oxidation of Mia40 by the sulfhydryl oxidase Erv1p. Mia40 in turn introduces disulfide bonds into folding proteins. A similar pathway exists in the periplasm of prokaryotes via DsbA and DsbB except that DsbB is not a sulfhydryl oxidase.

During disulfide bond formation many non-native disulfide bonds may be formed. Hence in vitro in a glutathione redox buffer, and probably in vivo for many proteins, the rate-limiting step for native disulfide bond formation is late-stage isomerization reactions, where disulfide bond isomerization is linked to conformational changes in protein substrates with substantial regular secondary structure. These steps are catalysed by thiol-disulfide isomerases, in particular in the ER by proteins belonging to the PDI-family and in the periplasm of prokaryotes by DsbC and DsbG.

Currently proteins that contain disulfide bonds are difficult for the biotech industry to produce on a large scale. The most common route is to produce these proteins in the cytoplasm of *E. coli*. Here there are no mechanisms for disulfide bond formation. Due to this the recombinant proteins are unable to attain their native conformation and form insoluble inclusion bodies. Inclusion body refolding is a widely studied and widely patented field. However, it is costly, complex and generally inefficient. Alternative routes for producing disulfide bonded proteins also have drawbacks.

I. Disulfide bond formation in the periplasm of *E. coli*. While native *E. coli* disulfide bond containing proteins fold efficiently in the periplasm, the yields of heterologously expressed proteins are often very low, in part due to the small size of the periplasm. In addition, the outer membrane of *E. coli* is freely diffusible to most small molecules which mean that the biophysical environment of the periplasm is very dependent on the external media.

II. Disulfide bond formation in the cytoplasm of modified *E. coli*. *E. coli* has two pathways to ensure that its cytoplasm is reducing: i) using thioredoxins/thioredoxin reductases and ii) using glutathione/glutaredoxin/glutathione reductase (see FIG. 2). When both pathways are knocked out, for example in the commercial origami or rosetta-gami strains (Novagen®), the cytoplasm is less reducing and disulfide bonds form in proteins. However, disulfide bond formation is still slow and inefficient. In addition, these strains are less genetically stable and grow significantly more slowly than wild type strains. While some disulfide bond containing proteins can be formed in the cytoplasm of origami or rosetta-gami (and equivalent), the yields of most proteins are below that required for commercial production.

III. Disulfide bond formation in the ER of eukaryotic organisms such as *S. cerevisiae, Pichia pastoris*, insect cell culture or even mammalian cell culture is much more efficient than that in bacteria. However, there is the corresponding increase in costs associated with the growth of eukaryotic organisms and problems associated with the large scale production of proteins in cell culture.

WO 9907727 A1 (or U.S. Pat. No. 6,361,964) describes a method of increasing disulfide bond formation in a protein by expressing the protein in a host cell that also expresses an isolated nucleic acid that encodes an Ero1 polypeptide or optionally an Ero1 polypeptide together with a protein disulfide isomerase. The Ero1 polypeptide is suggested to be for use in eukaryotic expression systems, wherein Ero1 aids folding in the ER, or in vitro refolding reactions.

WO 2005061718 A1 describes a method for producing a heterologous protein in a host cell utilizing a 2 micron-family plasmid. The host cell is cultured in such conditions that allow the expression of the gene encoding the fungal molecular chaperone or protein folding catalyst, such as Ero1 or protein disulfide isomerase, and the gene encoding a heterologous protein. The method uses 2 micron-family plasmids which can be applied only to eukaryotic cells. Both the protein and the molecular chaperone or protein folding catalyst such as Ero1 are targeted to the ER.

WO 2009058956 A1 describes a method for expressing a protein in a filamentous fungal host, wherein Ero1 can be co-expressed with the desired protein. Ero1 facilitates the folding of the desired protein in the ER.

KR 20070041166 A describes a method for producing a protein in the ER of a yeast cell, wherein Ero1 and protein disulfide isomerase are simultaneously expressed in a host cell.

Furthermore, U.S. Patent Application No. 2007/0193977 describes a method for producing a desired protein in a host cell comprising recombinant genes for a first and a second chaperone and for the desired protein. A preferred chaperone is PDI, in particular from fungal or mammalian origin. According to the publication various host expression systems including yeast, bacteria and mammalian cells may be used. Bacterial host cells are mentioned to be useful for cloning purposes.

Examples of commercial proteins that are produced by these various routes include insulin, tissue plasminogen activator, growth hormones and single chain antibodies. None of the mentioned patent publications disclose a prokaryotic expression system for the production of natively folded disulfide bond containing proteins.

SUMMARY

It is an object of the invention to provide a method for producing a natively folded disulfide bond containing protein in a prokaryotic host.

It is also an object of the invention to provide a host cell for producing a natively folded disulfide bond containing protein in a prokaryotic host.

Further, it is also an object of the present invention to provide a vector system for producing a natively folded disulfide bond containing protein in a prokaryotic host. These and other objects together with the advantages thereof over known methods, hosts and vectors, are achieved by the present invention as hereinafter described and claimed.

The invention is based on the use of genetic engineering of prokaryotic host cells to cytoplasmically express a sulfhydryl oxidase.

In one aspect, the present invention provides a method for producing a protein of interest containing one or more disulfide bonds in its native state in a prokaryotic host.

In one embodiment the invention provides a method which comprises that a prokaryotic host cell is genetically engineered to express the protein of interest and a sulfhydryl oxidase in the cytoplasm of the host cell, said protein of interest being formed in a soluble form and containing disulfide bonds due to the presence of the sulfhydryl oxidase in the cytoplasm of said host cell.

In one embodiment of the invention the protein product comprising the protein of interest is recovered from the cell culture or from the host cells and optionally purified.

In another aspect, the present invention provides a prokaryotic host cell for producing a protein of interest containing one or more disulfide bonds in its native state in a prokaryotic host.

In one embodiment the invention provides a prokaryotic host cell for producing a protein of interest containing natively folded disulfide bonds, which comprises that the host cell is genetically engineered to express a sulfhydryl oxidase and a protein of interest in the cytoplasm of the host cell.

In one preferred embodiment of the invention the sulfhydryl oxidase is co-expressed with the protein of interest.

In another preferred embodiment the sulfhydryl oxidase is expressed prior to the protein of interest.

In one further preferred embodiment, the prokaryotic host cells are engineered to express also a thiol-disulfide isomerase in the cytoplasm.

In one still further preferred embodiment the thiol-disulfide isomerase is the eukaryotic ER-resident enzyme protein disulfide isomerase (PDI).

In one further preferred embodiment the thiol-disulfide isomerase is DsbC, which is usually targeted to the periplasm of prokaryotes.

These co-expressions may be used separately or in combination with any of the other variations described herein, so long as a sulfhydryl oxidase is expressed in the host cell.

The host can be any prokaryotic host. In one embodiment of the invention, the prokaryotic host is a bacterial host, in one specific embodiment a gram-negative host, such as *E. coli*.

In one further preferred embodiment, expression of the disulfide bond containing protein of interest is achieved by expressing the protein as a genetic fusion with a fusion partner. This may be used separately or in combination with any of the other variations described herein, so long as a sulfhydryl oxidase is expressed in the host cell.

In one further embodiment the host cell may be deficient in thioredoxin reductase or glutathione reductase activity. This may be caused by having a mutation or deletion in trxB gene and/or a mutation or deletion in gor gene. These deficiencies may be used separately or in combination with any of the other variations described herein, so long as a sulfhydryl oxidase is expressed in the host cell.

In still further embodiments, codon usage for the nucleotide sequence encoding the protein may be optimized for expression in a particular host or the host codon usage manipulated so as to optimize expression of the recombinantly expressed protein. This may be done for example by supplementing the expression host's tRNA levels by production of tRNA species encoded by engineered plasmids. Codon usage may also be optimized for the sulfhydryl oxidase and/or the thiol-disulfide isomerase. These modifications may be used separately or in combination with any of the other variations described herein, so long as a sulfhydryl oxidase is expressed in the host cell.

The present invention provides also a vector system, comprising one or more vectors encoding sulfhydryl oxidase and the protein of interest, and optionally also, a thiol-disulfide isomerase. The proteins may be separately inducible.

Hence the invention has possible alternative solutions, all with the common factor of cytoplasmic expression of a sulfhydryl oxidase.

The method of the present invention results in the formation of native disulfide bonds in a significant proportion. The method is particularly suitable for expressing proteins where a biological activity is dependent on the formation of one or more intra- or inter-chain disulfide bonds.

In the following, the invention will be examined more closely with the aid of a detailed description and with reference to some working examples.

BRIEF DESCRIPTION OF THE FIGURES

FIG. 1 shows pathways for disulfide bond formation in: Panel A: The endoplasmic reticulum; Panel B: The intermembrane space of mitochondria (protein names given for the system in *Saccharomyces cerevisiae*); Panel C: The periplasm of prokaryotes (protein names given for the system in *Escherichia coli*).

FIG. 3 shows protein sequences of representative members of the ERO1 family of sulfhydryl oxidases (EC 1.8.4.-). The cleavable signal sequences are underlined. Endoplasmic oxiodreductin-1 from *Saccharomyces cerevisiae* corresponds to SEQ ID NO: 1; Human ERO1-like protein alpha corresponds to SEQ ID NO:2l and Human ERO1-like protein beta corresponds to SEQ ID NO:3.

FIGS. 4A and 4B show protein sequences of representative members of the ERV/ALR sulfhydryl oxidase domain containing sulfhydryl oxidases (Enzyme classification: EC 1.8.3.2). The ERV/ALR domain sequences for each, as currently defined in UniProt, are underlined. FIG. 4B shows also protein sequences of thiol-disulfide isomerases (EC 5.3.4.1) PDI and DsbC. The signal sequences are underlined. In FIG. 4 A, Human ALR corresponds to SEQ ID NO:4, *S. cerevisiae* mitochondrial FAD-like sulfhydryl oxidase ERV1 corresponds to SEQ ID NO:5, *S. cerevisiae* FAD like sulfhydryl oxidase ERV2 corresponds to SEQ ID NO6, and Human sulfhydryl oxidase 1 corresponds to SEQ ID NO:7. In FIG. 4B Human sulfhydryl oxidsase 2 corresponds to SEQ ID NO:8, Vaccinia virus FAD-linked sulfhydryl oxides E10 corresponds to SEQ ID NO5, *E. coli* DsbC corresponds to SEQ ID NO:10 and Human PDI corresponds to SEQ ID NO:11.

SEQUENCE LISTING

Figure 2:
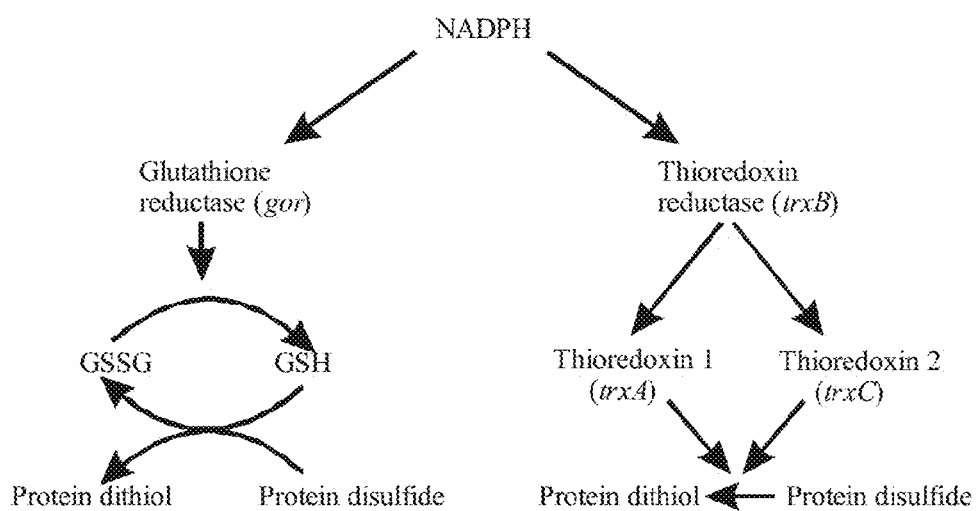
FIG. 2 shows the pathways for reducing disulfide bonds in the cytoplasm of *E. coli*. Gene names are given in parentheses. In commercial strains for the production of disulfide bonded proteins, such as origami and rosetta-gami (Novagen®), both the thioredoxin and glutathione pathways are knocked out by gor and trxB deletions or knock-outs by transposon mutagenesis.

The sequence listing includes the sequences:
SEQ ID NO:1 Endoplasmic oxidoreductin-1 from *Saccharomyces cerevisiae* (Swiss-Prot ID Q03103)
SEQ ID NO:2 Human ERO1-like protein alpha (Swiss-Prot ID Q96HE7)
SEQ ID NO:3 Human ERO1-like protein beta (Swiss-Prot ID Q86YB8)
SEQ ID NO:4 Human ALR (Swiss-Prot ID P55789)
SEQ ID NO:5 *S. cerevisiae* mitochondrial FAD-linked sulfhydryl oxidase ERV1 (Swiss-Prot ID P27882)
SEQ ID NO:6 *S. cerevisiae* FAD-linked sulfhydryl oxidase ERV2 (Swiss-Prot ID Q12284)
SEQ ID NO:7 Human sulfhydryl oxidase 1 (QSOX; Swiss-Prot ID O00391)
SEQ ID NO:8 Human sulfhydryl oxidase 2 (Swiss-Prot ID Q6ZRP7)
SEQ ID NO:9 Vaccinia virus FAD-linked sulfhydryl oxidase E10 (Swiss-Prot ID P21050)
SEQ ID NO:10 *E. coli* (K12 strain) DsbC
SEQ ID NO:11 Human PDI
SEQ ID NO: 12 hexa-histidine tag MHHHHHHM)
SEQ ID NO: 13 linker sequence NSSSNNNNHM
SEQ ID NO:14 linker sequence GSGSGSGSGSIEGRGSGSGSGSGSHM

DETAILED DESCRIPTION OF THE INVENTION

Definitions

"GSH" means reduced glutathione, a tripeptide called also γ-glutamylcysteinylglycine.

"GSSG" means oxidized glutathione. In GSSG two GSH's are linked by a disulfide bond.

"Oxidases" mean here enzymes that can use molecular oxygen to oxidize a (bio)chemical compound.

"Thioredoxins" mean enzymes that catalyse the reduction of disulfide bonds, which are often found in protein substrates. Thioredoxin is reduced in turn by thioredoxin reductase.

"Glutaredoxins" mean enzymes that catalyse the removal of glutathione from glutathione-protein mixed disulfides using reduced glutathione and generating oxidized glutathione, which in turn is reduced by glutathione reductase.

"PDI" mean protein disulfide isomerase. PDI's are enzymes which catalyse thiol-disulfide exchange reactions in the endoplasmic reticulum (ER) of eukaryotes. They belong to the thioredoxin superfamily.

"Dsb" mean disulfide bond forming enzymes. Dsb's are enzymes which catalyse thiol-disulfide exchange reactions in the periplasm of prokaryotes. DsbA, DsbC and DsbG belong to the thioredoxin superfamily. DsbB and DsbD are not thiol-disulfide isomerases.

Thioredoxin superfamily members are for example thioredoxins, protein disulfide isomerases (PDI's) and disulfide bond forming enzymes (Dsb's).

The present invention relates to a method for producing a natively folded disulfide bond containing protein in a prokaryotic host. The method comprises that a prokaryotic host cell is genetically engineered to express the protein of interest and a sulfhydryl oxidase in the cytoplasm of the host cell. The protein of interest is formed in a soluble form and contains disulfide bonds due to the presence of the sulfhydryl oxidase in the cytoplasm of said host cell. The present invention relates also to a prokaryotic host cell and a vector system for producing a protein of interest containing natively folded disulfide bonds.

A common prejudice in the field has been that the cytoplasm of most prokaryotes is reducing and therefore one cannot make disulfide bond containing proteins in the cytoplasm of a prokaryotic host unless the pathways for the reduction of disulfide bonds are disrupted or deleted, such as a ΔtrxB/Δgor strain. No one has disclosed introducing an active catalyst of de novo disulfide bond formation into the cytoplasm of a prokaryotic host.

Pathways for disulfide bond formation in the endoplasmic reticulum, inter-membrane space of mitochondria and periplasm of prokaryotes are shown in FIG. 1. Multiple pathways for dithiol oxidation to a disulfide in a folding protein exist. Direct oxidation by molecular oxygen, while widely used in vitro, is too slow to have physiological significance in native disulfide bond formation in vivo.

In the ER, PDI family members and GSSG can both introduce disulfide bonds into folding proteins, but both need to be reoxidised to complete the catalytic cycle. Oxidation of both PDI-family members and glutathione by molecular oxygen is too slow to have physiological significance in native disulfide bond formation in vivo. PDI is thought to be reoxidised by the sulfhydryl oxidase activity of Ero1-family members while the source of GSSG is under debate in the literature. The hydrogen peroxide made by Ero1 each catalytic cycle has the potential to oxidise dithiols in substrate proteins, to oxidise reduced glutathione to GSSG, to oxidise the active site of PDI family members and to form the regulatory disulfides in Ero1 and hence shut down peroxide production.

In the inter-membrane space of mitochondria of *Saccharomyces cerevisiae* Mia40 introduces disulfide bonds into folding proteins. To complete the catalytic cycle Mia40 is reoxidised by the sulfhydryl oxidase Erv1p. The direct formation of disulfide bonds in folding proteins or in Mia40 by molecular oxygen is too slow to have physiological significance in native disulfide bond formation in vivo. The potential parallel role of glutathione in disulfide bond formation in the inter-membrane space of mitochondria is unknown.

In the periplasm DsbA introduces disulfide bonds into folding proteins. To complete the catalytic cycle DsbA is reoxidised by the transmembrane protein DsbB. Unlike Ero1-family members or Erv1p, DsbB does not have sulfhydryl oxidase activity. The direct formation of disulfide bonds in folding proteins or in DsbB by molecular oxygen is too slow to have physiological significance in native disulfide bond formation in vivo. The potential parallel role of glutathione in disulfide bond formation in the periplasm is under debate in the literature.

Herein, by "protein of interest" are meant in particular proteins produced recombinantly in a foreign host. The proteins contain one or more disulfide bonds in their native state which are required to attain their native conformation. Many such proteins when expressed in a system in which disulfide bond formation is limited form insoluble inclusion bodies within the host. A protein of interest is here typically a eukaryotic protein, usually a mammalian protein, in particular a human protein.

The protein may have in its native state multiple disulfide bonds. The method of the present invention is particularly suitable for producing a protein having in its native state two or more disulfide bonds.

By "a host" or "a foreign host" is meant here in particular a prokaryotic host. More specifically the host can be a bacterial host, in particular a gram negative host, such as Escherichia coli (E. coli). In one preferred embodiment the host is E. coli.

According to this disclosure it is possible to produce a natively folded disulfide bond containing protein in a prokaryotic host. According to a preferred embodiment of the invention the protein may be recovered and optionally purified from the cultured host cells. The protein may be lyophilized or formulated with a carrier or diluents, if needed.

The advantage of the present invention is that the protein of interest is formed in soluble form. Typically no denaturation and renaturation steps of the protein are needed. Furthermore, the protein is produced directly in biologically active form.

Commercially significant proteins which may be produced by using the present invention comprise for example insulin, blood coagulation factors, cytokines, chemokines, interferons, growth hormones and single chain antibodies.

In this disclosure as examples of such proteins are the luminal domain of human tissue factor, E. coli alkaline phosphatase and phytase, bovine pancreatic trypsin inhibitor (BPTI), human colony stimulating factor 3 (CSF3), bone morphogenic protein 4 (BMP4), tissue plasminogen activator (t-PA), interferon α2, interleukin 6, interleukin 17, resistin and growth hormone 1.

In this disclosure the ability to generate "soluble protein" or "insoluble inclusion bodies" is deduced from SDS-PAGE analysis of total and soluble fractions of a cell lysate. The generation of insoluble inclusion bodies is a common occurrence when proteins that natively contain disulfide bonds are expressed in the cytoplasm of prokaryotic hosts. The formation of disulfide bonds allows protein folding to occur and hence allows the formation of soluble protein.

In this disclosure the "number of disulfide bonds" is deduced from the total number of cysteines in the protein and the number of cysteines free to react with iodoacetamide, as determined from mass spectrometric analysis after treatment of the protein with iodoacetamide. The reaction of a thiol group with iodoacetamide adds 57 Da to the mass of the protein.

In this disclosure the "biological activity" of a protein is deduced by well known methods in the art appropriate for the individual proteins being assayed. The biological activity or function of a protein reflects characteristics of the protein that result from the structure and conformational flexibility of the protein. These in turn are often dependent on the formation of native disulfide bonds. Hence biological activity, for example the ability of an enzyme to catalyze a specific enzymatic activity, is a measure of the attainment of the formation of native disulfide bonds within a protein.

The present invention provides a method for the production of proteins that require disulfide bond formation to reach their native biologically active conformation. The methods presented are particularly suitable for the expression of biologically active proteins that require the formation of multiple disulfide bonds. By multiple disulfide bonds is here meant two or more than two, typically more than three disulfide bonds.

By "a sequential disulfide bond" is meant a covalent linkage between the sulfur atoms of two cysteine residues in a protein which do not have an intervening cysteine residue in the primary sequence of the protein which is involved in another disulfide bond.

By "a non-sequential disulfide bond" is meant a covalent linkage between the sulfur atoms of two cysteine residues in a protein which have an intervening cysteine residue in the primary sequence of the protein which is involved in another disulfide bond.

The present invention is based on the use of pre- or co-expression of a sulfhydryl oxidase in the cytoplasm of prokaryotic bacteria, preferably of gram-negative bacteria such as E. coli, to generate disulfide bonds in folding proteins. As used herein, "sulfhydryl oxidases" refer to enzymes which use molecular oxygen to catalyze the reaction:

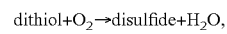
dithiol+O$_2$→disulfide+H$_2$O,

Since hydrogen peroxide (H$_2$O$_2$) is an oxidant that can be used to make disulfide bonds the overall reaction can also be written:

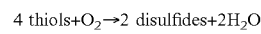
4 thiols+O$_2$→2 disulfides+2H$_2$O

In addition, some sulfhydryl oxidases, such as Erv1, are reported also to be able to transfer electrons to the cytochrome respiratory chain in mitochondria instead of using molecular oxygen as the acceptor.

Sulfhydryl oxidases comprise proteins such as Ero1, Erv1, Erv2, QSox, ALR etc. These enzymes use FAD as a cofactor and contain one, or more, redox active disulfide bonds. They fall into two families:
  i) the Ero family (Enzyme classification: EC 1.8.4.-) which are endoplasmic reticulum located sulfhydryl oxidases and which comprises, but is not limited to, the following exemplary members (see FIG. 3 for sequences): Endoplasmic oxidoreductin-1 from Saccharomyces cerevisiae (Swiss-Prot ID Q03103; for example as Genbank accession number CAA90553) (SEQ ID NO:1), human ERO1-like protein alpha (Swiss-Prot ID Q96HE7; for example as Genbank accession numbers AAF35260 or AAQ88828 or BAF85528 or AAH08674 or AAH12941) (SEQ ID NO:2), and human ERO1-like protein beta (Swiss-Prot ID Q86YB8; for example as Genbank accession numbers AAF97547 or CAI23525 or CAI14420 or AAH32823 or AAH44573) (SEQ ID NO:3);
  ii) proteins which contain an ERV/ALR sulfhydryl oxidase domain (Enzyme classification: EC 1.8.3.2). These proteins are found in a variety of cellular compartments including mitochondria and the secretory pathway. They include, but are not limited to, the following exemplary members (see FIG. 4 for sequences): Human ALR (Swiss-Prot ID P55789; for example as Genbank accession numbers AAG38105)

(SEQ ID NO:4), *Saccharomyces cerevisiae* mitochondrial FAD-linked sulfhydryl oxidase ERV1 (Swiss-Prot ID P27882; for example as Genbank accession numbers CAA97017) (SEQ ID NO:5), *Saccharomyces cerevisiae* FAD-linked sulfhydryl oxidase ERV2 (Swiss-Prot ID Q12284; for example as Genbank accession numbers CAA94987 or CAA92143) (SEQ ID NO:6), Human sulfhydryl oxidase 1 (QSOX; Swiss-Prot ID O00391; for example as Genbank accession numbers AAC09010 or AAQ89300 or CAI14838 or AAI00024) (SEQ ID NO:7), Human sulfhydryl oxidase 2 (Swiss-Prot ID Q6ZRP7; for example as Genbank accession numbers CAI16881 or CAM28352) (SEQ ID NO:8) and Vaccinia virus FAD-linked sulfhydryl oxidase E10 (Swiss-Prot ID P21050; for example as Genbank accession number AAA48051) (SEQ ID NO:9).

Within the scope of the present invention are proteins comprising any of the amino acid sequences of the above listed Genbank accession numbers or any of the amino acid sequences SEQ ID NO: 1 to 9, or a fragment of said sequences or a modified version of said sequences, which sequences still have sulfhydryl oxidase activity.

"A modified protein" refers to a protein wherein at one or more positions there have been amino acid insertions, deletions, or substitutions, either conservative or nonconservative, provided that such changes result in a protein still having sulfhydryl oxidase activity.

By "conservative substitutions" are meant here combinations, such as Val, Ile, Leu, Ala, Met; Asp, Glu; Asn, Gln; Ser, Thr, Gly, Ala; Lys, Arg, His; and Phe, Tyr, Trp. Preferred conservative substitutions comprise Gly, Ala; Val, Ile, Leu; Asp, Glu; Asn, Gln; Ser, Thr, Lys, Arg; and Phe, Tyr.

A modified version (or variant) of the sulfhydryl oxidase comprises typically an amino acid sequence having at least 25%, preferably at least 40%, more preferably at least 50%, still more preferably at least 60%, still and still more preferably at least 70%, more and more preferably at least 90% identity, most preferably at least 95%, or at least 98% identity to any of the amino acid sequences of the above listed Genbank accession numbers or to any of the amino acid sequences SEQ ID NO: 1 to 9.

In addition to full length sulfhydryl oxidases, shorter fragments may be used as long as they retain sulfhydryl oxidase activity. A fragment refers to a protein having at one or more positions deletions. The fragment may comprise at least 30%, at least 40%, at least 50%, preferably at least 60%, more preferably at least 70%, still more preferably at least 80%, more and more preferably at least 90%, or at least 95% of the complete amino acid sequence of the proteins.

By the term "identity" is here meant the identity between two amino acid sequences compared to each other from the first amino acid encoded by the corresponding gene to the last amino acid. Preferably the identity is measured by comparing the amino acid sequences without the sequences of any signal peptide the protein may have. The identity of the full-length sequences may be measured for example by using sequence analysis software, for example BLAST software available from the National Library of Medicine.

According to other preferred embodiments of the invention, the sulfhydryl oxidase of the invention is encoded by a nucleic acid sequence hybridizing under low or under high stringent conditions to nucleic acid sequences encoding amino acid sequences of the above listed Genbank accession numbers or amino acid sequences SEQ ID NO: 1 to 9. By high stringency conditions are meant conditions as disclosed for example in Ausubel et al. Current Protocols in Molecular Biology, 1996, Wiley Sons, New York, N.Y. High stringency hybridization conditions may comprise hybridization at about 42° C. and about 50% formamide, a first wash at about 65° C., about 2×SSC, and 1% SDS, followed by second wash at about 65° C., and about 0.1% SDS, 1×SSC. Lower stringency hybridization conditions may comprise hybridization at about 42° C. in the absence of formamide, a first wash at about 42° C., about 6×SSC, and 1% SDS, followed by second wash at about 50° C., about 6×SSC and about 1% SDS. Within the scope of the present invention are also nucleic acid sequences encoding the proteins comprising any of the amino acid sequences of the above listed Genbank accession numbers or any of the amino acid sequences SEQ ID NO: 1 to 9, or nucleic acid sequences encoding a fragment of said sequences or a modified version of said sequences, which sequences still have sulfhydryl oxidase activity. Suitable nucleic acid sequences encoding proteins having sulfhydryl oxidase activity are publicly available and can be found in gene banks.

Within the scope of the present invention are any enzymes with sulfhydryl oxidase activity. In particular, within the scope of the present invention are sulfhydryl oxidases comprising ERV/ALR sulfhydryl oxidase domain, in particular Erv1.

Within the scope of the invention are sulfhydryl oxidases belonging to Ero1 family proteins, in particular Ero 1, which is an ER-resident protein having an N-terminal signal sequence, the signal sequence should be removed before cytoplasmic expression is possible. Ero1 has multiple disulfide bonds which are required for it to function. It cannot fold to an active state in the cytoplasm of wild-type prokaryotes. Therefore, modifications, such as making the host cell deficient in thioredoxin reductase and/or glutathione reductase activity are needed to obtain functional protein, or preferentially the pre-expression of another sulfhydryl oxidase such as Erv1p will generate functional Ero1 in the cytoplasm. Ero1 works in the endoplasmic reticulum of eukaryotes, a compartment which has a significantly more oxidizing redox state than the cytoplasm. This arises due to the presence of oxidized glutathione. In the cytoplasm any oxidized glutathione made (by any route) is reduced by glutathione reductase (the gor gene product).

The present invention has been exemplified here by using the *Saccharomyces cerevisiae* enzyme Erv1p. Erv1p is a 189 amino acid FAD-dependent sulfhydryl oxidase that catalyzes disulfide bond formation. It is required for the import and folding of small cysteine-containing proteins in the mitochondrial inter-membrane space and is thought to form a redox cycle with Mia40.

In addition to wild type sulfhydryl oxidases, mutants may be used as long as they retain sulfhydryl oxidase activity.

In addition to wild type sulfhydryl oxidases, chimeric fusion proteins may be used as long as they retain sulfhydryl oxidase activity.

Sulfhydryl oxidase according to the present disclosure is produced in soluble and biologically active form in the cytoplasm of the prokaryotic host.

Furthermore, sulfhydryl oxidase according to the present disclosure is typically capable of functioning without a partner protein e.g. Erv1p can function without Mia40.

The present invention provides also a vector system comprising
- a vector encoding a protein of interest, or having an insertion site for a nucleic acid sequence encoding a protein of interest, and a sulfhydryl oxidase, or
- a first vector encoding a protein of interest, or having an insertion site for a nucleic acid sequence encoding a protein of interest, and
- a second vector encoding a sulfhydryl oxidase.

According to the present disclosure the vector or vectors are constructed to be capable of expressing the protein of interest and the sulfhydryl oxidase in the cytoplasm of the prokaryotic host cell.

The system may further comprise a vector encoding a thiol-disulfide isomerase in the cytoplasm of the prokaryotic host cell.

The vector encoding a thiol-disulfide isomerase may be the same vector encoding the sulfhydryl oxidase and/or the protein of interest.

The vector system can be introduced to a suitable prokaryotic host cell and the host can be cultured to produce a protein of interest comprising natively folded disulfide bonds.

The vector or vectors comprise a nucleic acid sequence (a gene) encoding a protein of interest and a sulfhydryl oxidase, and possible a thiol-disulfide isomerase. Two or all of said nucleic acid sequences may be in the same vector or all of them may be in different vectors. The nucleic acid sequence may be linked to a nucleic acid sequence encoding a suitable part of a fusion protein, said nucleic acid construction encoding a fusion protein. The vector system furthermore comprises regulatory elements for multiplying and expressing the nucleic acid sequences in a prokaryotic host. Each mRNA produced from the vector(s) may be separately inducible. The vector system may comprise also selection markers.

Host cells comprising the expression vector encoding the sulfhydryl oxidase and a protein of interest are cultured to produce the protein of interest in a biologically active form. Any suitable expression vector may be used. It is preferable that the vector contains an appropriate selection marker. It is also preferable that the vector contains a system for inducing expression.

Methods for cloning the genes of interest into appropriate vectors and culturing prokaryotic organisms are well known in the art.

The construction of suitable vectors has been exemplified here in the examples which report the use of pET23 and pLysS plasmid derivatives. These have ampicillin and chloramphenicol selection markers, respectively. T7 and arabinose inducible expression systems were used.

Any suitable culture media may be used for the cultivation of the prokaryotic organisms. In the examples reported here Luria-Bertani Media (LB media) and M9 minimal media was used. Enbase media (Biosilta Oy) and autoinduction media has also successfully been used.

The protein may be obtained from the cultured cells in a soluble form by routine cell lysis methods.

Cell lysis has been exemplified here in the examples by performing the addition of 0.1 mg/ml lysozyme to the resuspended cell pellet followed by freeze-thawing.

The protein of interest can be isolated from the cell lysate in substantially pure form by methods well known in the art and that are appropriate for the individual proteins and final application, for example column chromatography, polyacrylamide electrophoresis, or HPLC analysis. This can include the addition of a fusion tag to the protein of interest to aid purification.

Useful purification methods have been exemplified here in the examples where N-terminal hexa-histidine or N-terminal maltose binding protein (MBP) tags were used to facilitate purification using immobilized metal affinity chromatography or amylose resin, respectively.

"A substantially pure protein" means a preparation which is at least 60% by weight (dry weight) the protein of interest. Preferably the preparation is at least 75%, more preferably at least 80%, still more preferably at least 90%, still more preferably at least 95%, most preferably at least 99% by weight of the protein of interest.

In some applications the protein product comprising the protein of interest may be used with the cell culture without recovery, isolation and/or without purification. In other applications the protein product comprising the protein of interest may be recovered from the cell culture or cell medium or from host cells with or without purification. Furthermore, in some applications the protein product or purified protein may be diluted or concentrated, or lyophilized.

This invention has multiple possible alternative solutions. In one embodiment polycistronic vectors may be used i.e. vectors in which a single mRNA encodes the protein of interest plus the sulfhydryl oxidase and, where necessary, the thiol-disulfide isomerase (see FIG. 5). The order of the genes on polycistronic vectors does not affect the ability to co-expression of the proteins.

Figure 5:
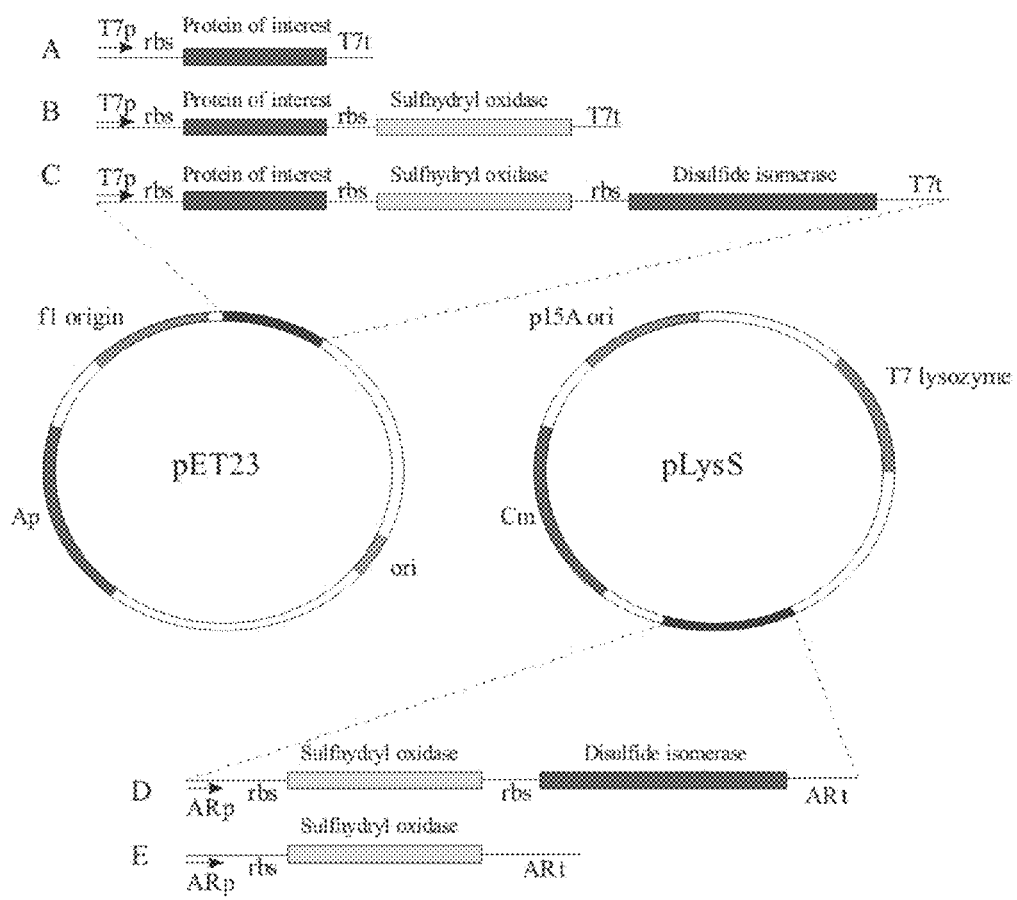
FIG. 5 shows plasmids pET23 and pLysS as modified for producing natively folded disulfide bond containing proteins in these studies. The order of the genes on polycistronic vectors does not affect the ability to co-expression of the proteins.

In another embodiment, the sulfhydryl oxidase, and where necessary the thiol-disulfide isomerase, are on separate vector from the protein of interest (see FIG. 5). The use of a two vector system allows for separate induction.

According to a preferred embodiment of the invention the vector or vectors is a plasmid or plasmids.

In one embodiment of the invention co-expression of a cytoplasmically expressed sulfhydryl oxidase with the protein of interest in wild type prokaryotic cells is undertaken. Disulfide bonds in the periplasm and in the ER are thought to form sequentially i.e. cysteine 1 is linked to cysteine 2, cysteine 3 to cysteine 4 etc. Hence proteins with a small number of sequential disulfide bonds should fold efficiently to their native state in the cytoplasm upon pre- or co-expression of a cytoplasmically expressed sulfhydryl oxidase. This is exemplified here with the efficient production of folded luminal domain of human tissue factor and *E. coli* alkaline phosphatase upon co-expression of the sulfhydryl oxidase (see examples 2 and 3). The sulfhydryl oxidase may be targeted to the cytoplasm by the removal of the N-terminal signal sequence where necessary.

In another embodiment of the invention, co-expression of a cytoplasmically expressed thiol-disulfide isomerase along with the sulfhydryl oxidase and the protein of interest is undertaken. For proteins with an increased number of sequential disulfide bonds there is a greater probability that incorrect disulfide bonds will form. The formation of incorrect disulfide bonds or the formation of non-sequential native disulfide bonds in the ER and periplasm is known to require the subsequent action of a thiol-disulfide isomerase to attain the native disulfide state of the protein of interest. Co-expression of such an isomerase, for example DsbC or PDI targeted to the cytoplasm, and combined with the expression of the sulfhydryl oxidase and the protein of interest increases the yield of natively folded protein. This has been exemplified with *E. coli* phytase (see example 4) and kringle t-PA (see example 6) and other proteins. The isomerases may be targeted to the cytoplasm by the removal of their N-terminal signal sequence.

Within the scope of the present invention are any enzymes with thiol-disulfide isomerase activity.

Preferred PDI sequences (Enzyme classification EC 5.3.4.1) comprise human PDI or yeast Pdi1p sequences. Yeast Pdi1p sequences can be found for example as Genbank accession numbers CAA42373 or BAA00723 or CAA38402.

Human PDI family members are for example PDI (for example as Genbank accession numbers CAA28775 or AAC13652 (SEQ ID NO:11)), ERp57 (for example as Genbank accession numbers BAA03759 or AAC51518), PDIp (for example as Genbank accession numbers BAE38734 or AAK61223), ERp72 (for example as Genbank accession numbers AAA58460 or AAH00425), PDILT (for example as Genbank accession numbers BAC05068 or AAH42607), ERp27 (for example as Genbank accession numbers AAQ88900 or AAH30218), PDIr (for example as Genbank accession number BAA08451), ERp28 (for example as Genbank accession numbers CAA64397 or CAG46468), Erdj5 (for example as Genbank accession numbers AF038503 or AK027696), P5 (for example as Genbank accession numbers BAA08450 or AAH01312), ERp18 (for example as Genbank accession numbers AF543416 or CAI17031), ERp44 (for example as Genbank accession numbers CAC87611 or AAQ89407), ERp46 (for example as Genbank accession numbers AAQ89009 or BAC11526), TMX (for example as Genbank accession numbers AAQ89003 or AK075395), TMX2 (for example as Genbank accession numbers AAD27740 or AAH00666), TMX3 (for example as Genbank accession numbers BAG53687 or AAH93792), TMX4 (for example as Genbank accession numbers AAQ89363 or BAC11599), hAG-2 (for example as Genbank accession numbers AAC77358 or AAQ89368) and hAG-3 (for example as Genbank accession numbers AAL55402 or AAH58284).

Sequences for DsbC (EC 5.3.4.1) can be found for example as Genbank accession numbers AAA83074 or AAC75931 (SEQ ID NO: 10).

The thiol-disulfide isomerases having N-terminal signal sequence can be expressed in the cytoplasm by the removal of the N-terminal signal sequence.

In addition to mature thiol-disulfide isomerases, shorter fragments or modified forms or chimeric proteins may be used as long as they retain thiol-disulfide isomerase activity.

Enzymes having thiol-disulfide isomerase activity may comprise fragments or modifications of the above amino acid sequences.

"A modified protein" refers to a protein wherein at one or more positions there have been amino acid insertions, deletions, or substitutions, either conservative or nonconservative, provided that such changes result in a protein still having thiol-disulfide isomerase activity.

A modified version (or variant) of the enzyme having thiol-disulfide isomerase activity comprises typically an amino acid sequence having at least 25%, preferably at least 40%, more preferably at least 50%, still more preferably at least 60%, still and still more preferably at least 70%, more and more preferably at least 90% identity, most preferably at least 95% or at least 98% identity to any of the above mentioned amino acid sequences.

In addition to full length enzyme having thiol-disulfide isomerase activity, shorter fragments may be used as long as they retain thiol-disulfide isomerase activity. A fragment refers to a protein having at one or more positions deletions. The fragment may comprise at least 30%, at least 40%, at least 50%, preferably at least 60%, more preferably at least 70%, still more preferably at least 80%, more and more preferably at least 90%, or at least 95% of the complete amino acid sequence of the proteins.

According to other preferred embodiments of the invention, the enzyme having thiol-disulfide isomerase activity of the invention is encoded by a nucleic acid sequence hybridizing under low or under high stringent conditions to nucleic acid sequences encoding the above mentioned amino acid sequences. By high stringency conditions are meant conditions as disclosed for example in Ausubel et al. Current Protocols in Molecular Biology, 1996, Wiley Sons, New York, N.Y. High stringency hybridization conditions may comprise hybridization at about 42° C. and about 50% formamide, a first wash at about 65° C., about 2×SSC, and 1% SDS, followed by second wash at about 65° C., and about 0.1% SDS, 1×SSC. Lower stringency hybridization conditions may comprise hybridization at about 42° C. in the absence of formamide, a first wash at about 42° C., about 6×SSC, and 1% SDS, followed by second wash at about 50° C., about 6×SSC and about 1% SDS.

Within the scope of the present invention are also nucleic acid sequences encoding the proteins comprising any of the amino acid sequences of the above gene bank accession numbers or the sequences SEQ ID NO:10 or SEQ ID NO:11 having thiol-disulfide isomerase activity, or nucleic acid sequences encoding a fragment of said sequences or a modified version of said sequences, which sequences still have thiol-disulfide isomerase activity. Suitable nucleic acid sequences encoding proteins having thiol-disulfide isomerase activity are publicly available and can be found in gene banks.

In another embodiment of the invention, the protein of interest is expressed as a fusion protein. Disulfide bond formation is the rate limiting step in protein folding in vitro and in vivo. If the folding protein misfolds and aggregates (forms inclusion bodies) before the sulfhydryl oxidase and/or thiol-disulfide isomerase can act on it then low yields of correctly folded protein will be obtained. The generation of a fusion protein between a well expressed and quickly folding protein and the protein of interest is known to often inhibit inclusion body formation. Well known in the art examples include maltose binding protein (MBP), glutathione S-transferase (GST) and thioredoxin (Trx). In the examples included here we used MBP. The use of this fusion protein technology combined with co-expression of the sulfhydryl oxidase increased the yield of soluble protein for human CSF3 and BMP4 (see example 5). When this technology was combined with co-expression of a thiol-disulfide isomerase as well it increased the soluble yields of kringle t-PA (see example 6) and other proteins.

In another embodiment of the invention, mutant prokaryotic cells are used. Usually the cytoplasm of E. coli is reducing and any disulfides that are formed can be reduced by thioredoxin/thioredoxin reductase and/or the glutathione/glutaredoxin/glutathione reductase systems while the protein is folding. To inhibit this, the expression of the sulfhydryl oxidase can be combined with knock-outs in these two pathways, for example the commercial rosetta-gami strain. When expression of the sulfhydryl oxidase was combined with the rosetta-gami strain background it increased the yields of active kringle tPA (see example 6) but decreased the yields of active alkaline phosphatase (see example 3) and phytase (see example 4).

In another embodiment of the system the sulfhydryl oxidase, and where appropriate a thiol-disulfide isomerase, are expressed prior to expression of the protein of interest.

The kinetic partitioning between productive folding and the formation of inclusion bodies is known to depend on the degree to which protein aggregates are already present in the system. Upon co-expression of a sulfhydryl oxidase with the protein of interest, the initial production of the protein of interest is effective in the absence of sulfhydryl oxidase, since both are being co-expressed. This increases the chances of initial aggregate formation which in turn becomes an auto-catalytic process. The pre-synthesis of the sulfhydryl oxidase, and thiol-disulfide isomerase if required, prior to the induction of synthesis of the protein of interest circumvents this problem and would be expected to increase the soluble biologically-active yields of the protein of interest. Suitable vectors based on pLysS with an arabinose induction system to enable this were constructed (see FIG. 5). This system is able to fold a range of proteins and increases the yield of active protein for example see kringle t-PA (example 6).

According to the present disclosure

The protein production system according to this disclosure increases production of active protein in prokaryotic hosts compared to wild type strains. The increase is over 100-fold in a wild-type E. coli background. The present system also gives circa 3 fold higher activity of protein of interest than the prior system (rosetta-gami strain). This has been here exemplified by expressing alkaline phosphatase, tPA and phytase in this system and in the commercial rosetta-gami strain.

The rosetta-gami strain is genetically unstable and grows much slower than the comparable wild-type strains. The use of wild type strains modified according to the present disclosure is more advantageous. Although, for some proteins the use of a strain being deficient in thioredoxin reductase or glutathione reductase activity and being modified according to the present disclosure, may be of advantage.

In addition to sulfhydryl oxidase the expression of disulfide isomerase may be of advantage, in particular if the protein of interest comprises non-sequential disulfide bonds or a large number of sequential disulfide bonds.

The more proteins that are required to be co-expressed, the smaller the amount of cellular resources available to make the protein of interest i.e. the system must always be kept to the simplest possible.

The more disulfide bonds the target protein has the higher the level of required expression of the sulfhydryl oxidase and the disulfide isomerase. However, too high a level of expression of either factor will result in a reduction in the levels of expression of the target protein (see above).

Target proteins with non-optimal codon-usage for E. coli production may require the co-expression of rare tRNA's for optimal production e.g. the use of the pLysS RARE plasmid (found in rosetta-gami along with the gor and trxB knockouts).

Target proteins that naturally have a pro-sequence generally may require the use of a fusion protein to keep them soluble during folding.

Various embodiments of the invention are described below with the aid of the following numbered clauses 1-19:

1. A method for producing a protein of interest containing one or more disulfide bonds in its native state, which comprises that a prokaryotic host cell is genetically engineered to express the protein of interest and a sulfhydryl oxidase in the cytoplasm of the host cell, said protein of interest being formed in a soluble form and containing disulfide bonds due to the presence of the sulfhydryl oxidase in the cytoplasm of said host cell.

2. The method according to clause 1, wherein the protein product comprising the protein of interest is recovered from the cell culture or from the host cells and optionally purified.

3. The method according to clause 1 or 2, wherein the protein of interest is co-expressed with the sulfhydryl oxidase.

4. The method according to any one of clauses 1 to 3, wherein the sulfhydryl oxidase is expressed prior to the protein of interest.

5. The method according to any one of the preceding clauses, wherein the host cells are engineered to further express a thiol-disulfide isomerase in the cytoplasm.

6. A prokaryotic host cell for producing a protein of interest containing natively folded disulfide bonds, which comprises that the host cell is genetically engineered to express a sulfhydryl oxidase and a protein of interest in the cytoplasm of the host cell.

7. The method or the host cell according to any one of the preceding clauses, wherein the sulfhydryl oxidase uses FAD as a cofactor and contains one, or more, redox active disulfide bonds.

8. The method or the host cell according to any one of the preceding clauses, wherein the sulfhydryl oxidase belongs to sulfhydryl oxidases comprising ERV/ALR sulfhydryl oxidase domain.

9. The method or the host cell according to any one of the preceding clauses, wherein the sulfhydryl oxidase belongs to ERO family of sulfhydryl oxidases.

10. The method or the host cell according to any one of the preceding clauses, wherein the host cell further expresses a thiol-disulfide isomerase in the cytoplasm.

11. The method or the host cell according to clause 10, wherein the disulfide isomerase is PDI, or DsbC.

12. The method or the host cell according to any one of the preceding clauses, wherein the prokaryotic host is a gram negative bacterium, such as E. coli.

13. The method or the host cell according to any one of the preceding clauses, wherein the protein of interest is produced as a fusion protein.

14. The method or the host cell according to any one of the preceding clauses, wherein the sulfhydryl oxidase and the disulfide isomerase are induced either separately or together with the protein of interest.

15. The method or the host cell according to any one of the preceding clauses, wherein the host cell is deficient in thioredoxin reductase and/or glutathione reductase activity.

16. A vector system for a prokaryotic host cell for producing a protein of interest containing natively folded disulfide bonds, which comprises a vector encoding a protein of interest, or having a site for a nucleic acid sequence encoding a protein of interest, and a sulfhydryl oxidase, or a first vector encoding a protein of interest, or having a site for a nucleic acid sequence encoding a protein of interest, and a second vector encoding a sulfhydryl oxidase, wherein said vector or vectors are constructed to be capable of expressing the protein of interest and the sulfhydryl oxidase in the cytoplasm of a prokaryotic host cell.

17. The vector system according to clause 16 for producing a protein of interest, wherein the system further comprises a vector encoding a thiol-disulfide isomerase, said vector being the same or different vector as the vectors in the vector system, and said vector being constructed to be capable of expressing a thiol-disulfide isomerase in the cytoplasm of the prokaryotic host.

18. The vector system according to clause 16 or 17, wherein the sulfhydryl oxidase and thiol-disulfide isomerase are induced either separately or together with the protein of interest.

19. A prokaryotic host cell system, which comprises the vector system according to any one of clauses 16 to 18.

The following non-limiting examples illustrate the invention.

EXAMPLES

Example 1

Plasmid constructs used in the protein expressions were generated as part of pre-studies (see FIG. 5). The original constructs were polycistronic with multiple genes encoded by a single mRNA driven by a T7 promoter system (IPTG inducible) in a modified version of pET23. These included the protein of interest alone (A), this plus the sulfhydryl oxidase (B) or plus the sulfhydryl oxidase and either PDI or DsbC as a thiol-disulfide isomerase (C).

Subsequent constructs had the sulfhydryl oxidase (D) or the sulfhydryl oxidase plus the thiol-disulfide isomerase (E) on an arabinose promoter as part of a modified version of pLysS. Constructs D and E are fully compatible with construct A and allow easy inter-conversion of the protein of interest in the system. In addition, constructs D and E allow pre-expression or co-expression of the sulfhydryl oxidase, or the sulfhydryl oxidase and thiol-disulfide isomerase, and the protein of interest.

Example 2

Efficient Production of the Luminal Domain of Human Tissue Factor

Tissue factor (TF), also known as thromboplastin factor III, is a protein involved in the coagulation of blood. It is a transmembrane protein whose luminal domain contains two sequential disulfide bonds.

pVD81, is a derivative of pET23a which has cloned into the multi-cloning site a gene encoding for an N-terminal hexa-histidine tag (MHHHHHM) (SEQ ID NO: 11) followed in frame with the luminal domain of human tissue factor (sTF) as represented by the fragment Ser 33-.Glu 251 of the full length protein. This vector expresses sTF upon induction with IPTG.

pVD77 is a derivative of pVD81, in which the gene for the sulfhydryl oxidase Erv1p from S. cerevisiae has been cloned (Met 1-Glu 189) (SEQ ID NO: 5) after the gene for sTF (with suitable ribosome binding sites to initiate translation of both; see FIG. 5). This polycistronic vector co-expresses sTF and Erv1p upon induction with IPTG.

E. coli strains transformed with these expression vectors were streaked out from glycerol stocks stored at −70° C. onto agar plates containing suitable antibiotics to allow for selection. The next day one colony from these plates were used to inoculate 5 mls of LB media, containing suitable antibiotics, and grown overnight at 30° C., 200 rpm. This overnight culture was used to seed a 50 mls culture of LB containing suitable antibiotics in a 250 ml flask to an optical density of 0.05 at 600 nm ($OD_{600}$). This culture was grown at 25° C., 200 rpm until the $OD_{600}$ reached 0.4 at which point protein production was induced by the addition of 1 mM IPTG. The cells were then grown for 4 hours at 25° C., 200 rpm and the final $OD_{600}$ measured. The cells were collected by centrifugation and resuspended to an $OD_{600}$ equivalent of 10 in 20 mM sodium phosphate pH 7.4, 20 μg/ml DNase, 0.1 mg/ml egg white lysozyme, and frozen. Cells were lysed by freeze-thawing. Where appropriate, the insoluble fraction was removed by centrifugation and the soluble fraction removed quickly to a new container.

Figure 6:
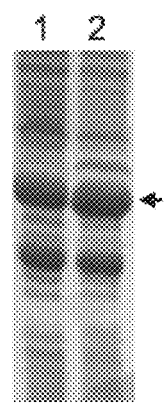
FIG. 6 shows representative SDS-PAGE from expression of the luminal domain of human tissue factor with co-expression with a sulfhydryl oxidase in LB media at 25° C. Lane 2 shows the total *E. coli* lysate, lane 1 shows the soluble fraction. The position of the luminal domain of tissue factor is marked with an arrow.

When sTF is expressed alone in the cytoplasm of the E. coli strain BL21 (DE3) pLysS the protein is unable to fold correctly and forms insoluble inclusion bodies. When a sulfhydryl oxidase is co-expressed at 25° C. with sTF in the cytoplasm of the same E. coli strain, sTF is made solubly in high yields. FIG. 6 shows representative SDS-PAGE from expression of sTF with co-expression with a sulfhydryl oxidase in LB media at 25° C. Lane 2 shows the total E. coli lysate, lane 1 shows the soluble fraction. The position of the luminal domain of tissue factor is marked with an arrow.

Purification of this protein via an N-terminal hexa-histidine tag followed by treatment with iodoacetamide and mass spectrometry analysis of the purified protein revealed the existence of no free thiol groups implying that two disulfide bonds had been formed in this system.

Example 3

Efficient Production of E. coli Alkaline Phosphatase

Alkaline phosphatase is a hydrolase which removes phosphate groups from many types of molecules. The bacterial enzyme folds in the periplasm. It has two sequential disulfide bonds whose formation is essential for activity. Since it is easily assayed bacterial alkaline phosphatase is widely used as a model protein for disulfide bond formation in vivo.

pVD80, is a derivative of pET23a which has cloned into the multi-cloning site a gene encoding for an N-terminal hexa-histidine tag (MHHHHHM) (SEQ ID NO:12) followed in frame with the mature form of E. coli alkaline phosphatase (PhoA) as represented by the fragment Arg 22-Lys 471 of the full length protein. This vector expresses alkaline phosphatase upon induction with IPTG.

pVD82 is a derivative of pVD80, in which the gene for the sulfhydryl oxidase Erv1p from S. cerevisiae has been cloned (Met 1-Glu 189) (SEQ ID NO: 5) after the gene for E. coli alkaline phosphatase (with suitable ribosome binding sites to initiate translation of both; see FIG. 5). This polycistronic vector co-expresses E. coli alkaline phosphatase and Erv1p upon induction with IPTG.

E. coli strains with these expression vectors were streaked out from glycerol stocks stored at −70° C. onto agar plates containing suitable antibiotics to allow for selection. The next day one colony from these plates were used to inoculate 5 mls of LB media, containing suitable antibiotics, and grown overnight at 30° C., 200 rpm. This overnight culture was used to seed a 50 mls culture of LB containing suitable antibiotics in a 250 ml flask to an optical density of 0.05 at 600 nm ($OD_{600}$). This culture was grown at 30° C., 200 rpm until the $OD_{600}$ reached 0.4 at which point protein production was induced by the addition of 1 mM IPTG. The cells were then grown for 4 hours at 30° C., 200 rpm and the final $OD_{600}$ measured. The cells were collected by centrifugation and resuspended to an $OD_{600}$ equivalent of 10 in 20 mM sodium phosphate pH 7.4, 20 μg/ml DNase, 0.1 mg/ml egg white lysozyme and frozen. Cells were lysed by freeze-thawing. Where appropriate, the insoluble fraction was removed by centrifugation and the soluble fraction removed quickly to a new container.

To monitor the production of active alkaline phosphatase we used the standard 4-nitrophenylphosphate assay at pH 8.0. This assay revealed that expression of alkaline phosphatase in the cytoplasm of *E. coli* resulted in the production of minimal active protein. In contrast co-expression of a sulfhydryl oxidase resulted in significant levels of soluble active protein (see FIG. 7).

Figure 7:
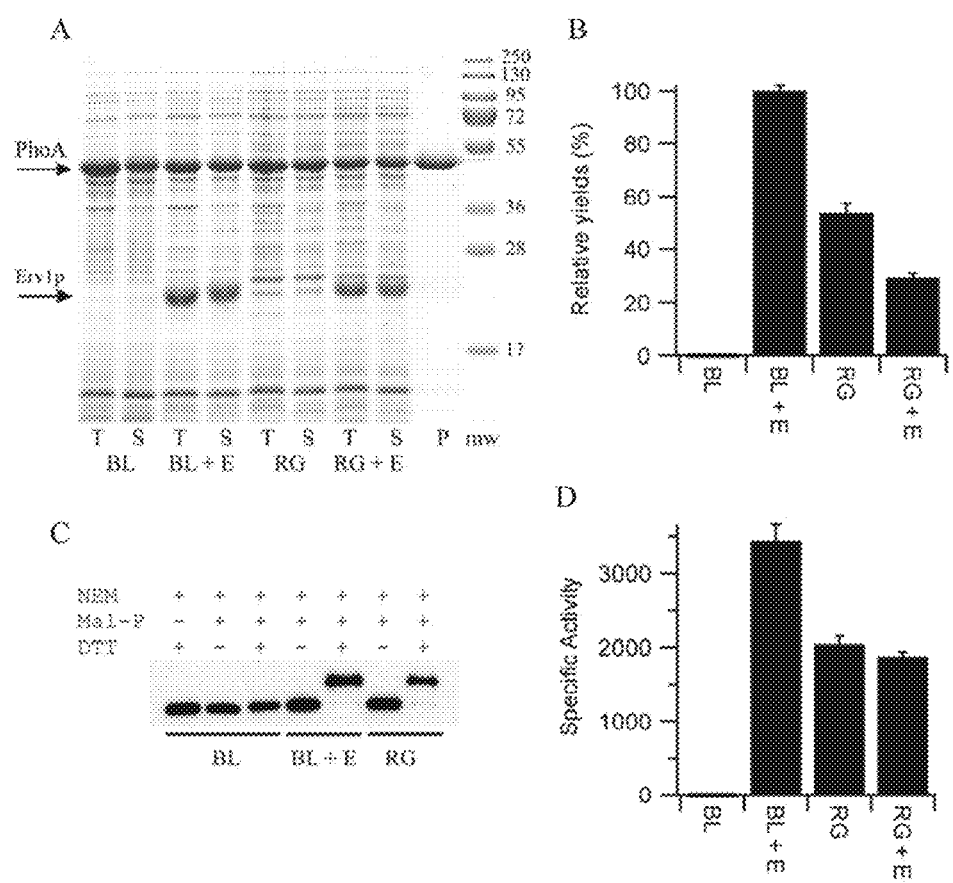
FIG. 7 shows production of PhoA in the cytoplasm of *E. coli* in LB media at 30° C. Panel A) SDS-PAGE analysis. Alternate lanes show total (T) and soluble (S) fractions. The final lanes show the purified protein from BL21 with co-expression of Erv1p and the molecular weight markers. The strains used were BL=BL21 (DE3) pLysRARE and RG=rosetta-gami; +E=co-expression of the sulfhydryl oxidase Erv1p from a polycistronic vector. The positions of PhoA and Erv1p are marked with arrows. Panel B). Measurements for the activity of *E. coli* alkaline phosphatase expressed in the cytoplasm of *E. coli* in LB media at 30° C. 4-nitrophenylphosphate used a s the substrate, pH of the reaction was 8.0 and the values are cited as relative activity (%) compared with the most active system which is BL21 (DE3) pLysSRARE+expression of the sulfhydryl oxidase. The strains used were BL=BL21 (DE3) pLysRARE and RG=rosetta-gami; +E=co-expression of the sulfhydryl oxidase Erv1p from a polycistronic vector. Panel C) Representative blot from a shift-assay based on alkylation of free thiol groups to examine the disulfide bond status of the PhoA produced. The samples are treated with the thiol-blocking agent N-ethylmaleimide (NEM) before reduction and maleimide based addition of polyethyleneglycol. Hence an increase in apparent molecular weight is consistent with the presence of one or more disulfide bonds in the original sample. Panel D) Specific activity (μmole of product formed per minute per mg of protein) of PhoA purified from *E. coli* strains with and without co-expression of a sulfhydryl oxidase. The data is shown as mean±s.d.

FIG. 7 shows production of PhoA in the cytoplasm of *E. coli* in LB media at 30° C. Panel A) SDS-PAGE analysis. Alternate lanes show total (T) and soluble (S) fractions. The final lanes show the purified protein from BL21 with co-expression of Erv1p and the molecular weight markers. The strains used were BL=BL21 (DE3) pLysRARE and RG=rosetta-gami; +E=co-expression of the sulfhydryl oxidase Erv1p from a polycistronic vector. The positions of PhoA and Erv1p are marked with arrows. Panel B). Measurements for the activity of *E. coli* alkaline phosphatase expressed in the cytoplasm of *E. coli* in LB media at 30° C. 4-nitrophenylphosphate used a s the substrate, pH of the reaction was 8.0 and the values are cited as relative activity (%) compared with the most active system which is BL21 (DE3) pLysSRARE+expression of the sulfhydryl oxidase. The strains used were BL=BL21 (DE3) pLysRARE and RG=rosetta-gami; +E=co-expression of the sulfhydryl oxidase Erv1p from a polycistronic vector. Panel C) Representative blot from a shift-assay based on alkylation of free thiol groups to examine the disulfide bond status of the PhoA produced. The samples are treated with the thiol-blocking agent N-ethylmaleimide (NEM) before reduction and maleimide based addition of polyethyleneglycol. Hence an increase in apparent molecular weight is consistent with the presence of one or more disulfide bonds in the original sample. The greater the number of disulfide bonds the greater the mass shift. PhoA produced in both the Δgor ΔtrxB background and in the wild-type background plus co-expression of Erv1p show a homogeneous disulfide bonded protein being produced, Panel D) Specific activity (μmole of product formed per minute per mg of protein) of PhoA purified from *E. coli* strains with and without co-expression of a sulfhydryl oxidase. The data is shown as mean±s.d.

Previously it had been shown that active alkaline phosphatase can be made in strains such as rosetta-gami in which the reducing pathways have been disrupted. Production of alkaline phosphatase in rosetta-gami resulted in the production of active protein, but circa two-fold less activity was seen than for the co-expression of the sulfhydryl oxidase in wild type *E. coli*.

Our system increases production of active protein over 100-fold in a wild-type *E. coli* background and gives circa 2 fold higher alkaline phosphatase activity than the commercial rosetta-gami strain.

Example 4

Efficient Production of *E. coli* Phytase

Phytase (AppA) is an *E. coli* protein with similar activity to alkaline phosphatase except that it has optimal activity under acidic pH values (hence one of its alternative names is acid phosphatase). The protein contains four disulfide bonds, one of which is non-sequential. As it contains a non-sequential disulfide bond it is used as a model protein for disulfide bond formation which requires isomerisation. It is also used as an important animal feed adduct.

pVD96, is a derivative of pET23a which has cloned into the multi-cloning site a gene encoding for an N-terminal hexa-histidine tag (MHHHHHHM) (SEQ ID NO:12) followed in frame with the mature form of *E. coli* Phytase (AppA) as represented by the fragment Gln 23-Leu 432 of the full length protein. This vector expresses phytase upon induction with IPTG.

pFH231 is a derivative of pVD96, in which the gene for the sulfhydryl oxidase Erv1p from *S. cerevisiae* has been cloned (Met 1-Glu 189) (SEQ ID NO: 5) after the gene for phytase (with suitable ribosome binding sites to initiate translation of both; see FIG. 5). This polycistronic vector co-expresses phytase and Erv1p upon induction with IPTG.

pFH244 is a derivative of pVD96, in which the gene for the mature form of DsbC from *E. coli* has been cloned (Asp 21-Lys 236) (SEQ ID NO: 10) after the gene for phytase (with suitable ribosome binding sites to initiate translation of both; see FIG. 5). This polycistronic vector co-expresses both phytase and mature DsbC upon induction with IPTG.

pFH233 is a derivative of pVD96, in which the gene for the sulfhydryl oxidase Erv1p from *S. cerevisiae* (Met 1-Glu 189) (SEQ ID NO:5) and the gene for the mature form of DsbC from *E. coli* (Asp 21-Lys 236) (SEQ ID NO:10) have been cloned after the gene for phytase (with suitable ribosome binding sites to initiate translation of both; see FIG. 5). This polycistronic vector co-expresses phytase, Erv1p and DsbC upon induction with IPTG.

*E. coli* strains with these expression vectors were streaked out from glycerol stocks stored at −70° C. onto agar plates containing suitable antibiotics to allow for selection. The next day one colony from these plates were used to inoculate 5 mls of LB media, containing suitable antibiotics, and grown overnight at 30° C., 200 rpm. This overnight culture was used to seed a 50 mls culture of LB containing suitable antibiotics in a 250 ml flask to an optical density of 0.05 at 600 nm ($OD_{600}$). This culture was grown at 30° C., 200 rpm until the $OD_{600}$ reached 0.4 at which point protein production was induced by the addition of 1 mM IPTG. The cells were then grown for 4 hours at 30° C., 200 rpm and the final $OD_{600}$ measured. The cells were collected by centrifugation and resuspended to an $OD_{600}$ equivalent of 10 in 20 mM sodium phosphate pH 7.4, 20 μg/ml DNase, 0.1 mg/ml egg white lysozyme and frozen. Cells were lysed by freeze-thawing. Where appropriate, the insoluble fraction was removed by centrifugation and the soluble fraction removed quickly to a new container.

To monitor the activity of phytase an assay similar to that employed for alkaline phosphatase was used using 4-nitro-phenylphosphate as the substrate (see example 3) except that the pH of the reaction was held at pH 2.5, the optimal for phytase activity.

Figure 8:
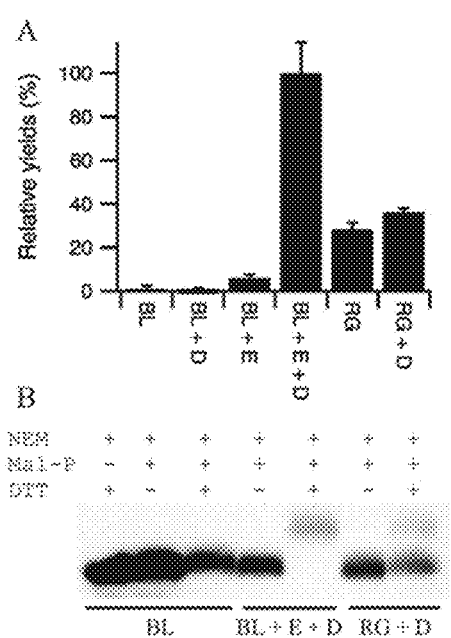
FIG. 8 shows production of AppA in the cytoplasm of *E. coli* strains in LB media at 30° C. Panel A) Measurements for the activity of *E. coli* phytase (AppA). Absorbance values were measured after quenching the reaction with sodium hydroxide (NaOH) and the values are cites as relative activity (%) compared with the most active system which is BL21 (DE3) pLysSRARE+expression of the sulfhydryl oxidase and DsbC. The background activity is subtracted. Strains used were BL=BL21 (DE3) pLysSRARE and RG=rosetta-gami. +=co-expression from a polycistronic vector where D=mature *E. coli* DsbC, E=*S. cerevisiae* Erv1p. Panel B) Representative blot from a shift-assay based on alkylation of free thiol groups to examine the disulfide bond status of the AppA produced.

FIG. 8 shows production of AppA in the cytoplasm of *E. coli* strains in LB media at 30° C. Panel A) Measurements for the activity of *E. coli* phytase (AppA). Absorbance values were measured after quenching the reaction with sodium hydroxide (NaOH) and the values are cites as relative activity (%) compared with the most active system which is BL21 (DE3) pLysSRARE+expression of the sulfhydryl oxidase and DsbC. The background activity is subtracted. Strains used were BL=BL21 (DE3) pLysSRARE and RG=rosetta-gami. +=co-expression from a polycistronic vector where D=mature *E. coli* DsbC, E=*S. cerevisiae* Erv1p. B) Representative blot from a shift-assay based on alkylation of free thiol groups to examine the disulfide bond status of the AppA produced. While AppA produced upon co-expression of Erv1p in a wild-type background shows a homogeneous disulfide bonded protein being produced, the protein produced in the Δgor ΔtrxB background shows heterogeneity and a lower degree of disulfide bond formation. Note that the molecular weight of the mal-PEG is not homogenous and hence modified proteins, especially those with multiple mal-PEG added, appear as more defuse bands. Over-expression of phytase in the cytoplasm of *E. coli* results in activity levels comparable with samples in which no phytase is expressed. In contrast co-expression of a sulfhydryl oxidase results in increased phytase activity (sample "BL+E"). Since phytase contains a non-sequential disulfide bond co-expression of a thiol-disulfide isomerase is required for optimal folding. Note however that in the wild type background expression co-expression of only a thiol-disulfide isomerase does not significantly increase the activity of phytase (samples "BL+D" such proteins only aid so long as a sulfhydryl oxidase is present (sample "BL+E+D" see FIG. 8).

The present invention increases production of active protein over 100-fold in a wild-type *E. coli* background and gives more activity than the current commercial rosetta-gami system.

Example 5

Efficient Production of Soluble Human CSF3 and Human BMP4

Colony stimulating factors (CSF) are hormones that cause cells to proliferate and differentiate. CFS3 stimulates the production of granulocytes and stem cells and is also known as granulocyte colony-stimulating factor. It is used in oncological and hematological applications and is made commercially under different names, including Neupogen and Religast. CSF3 contains two sequential disulfide bonds and one free thiol group near the N-terminal of the protein which probably results in non-native disulfide bond formation.

Bone morphogenic proteins (BMP) are a group of cytokines which induce the formation of bone and cartilage. BMP4 regulates the formation of teeth, limbs and bones and plays a role in fracture repair. It contains three non-sequential intramolecular disulfide bonds along with one intermolecular disulfide bond.

pVD109 is a polycistronic derivative of pET23a which has a gene encoding for a cytoplasmically targeted MBP tag (as represented by the fragment Lys 27-Thr 392 plus a linker encoding the amino acid sequence NSSSNNNNHM, SEQ ID NO: 13) followed in frame with the mature form of mature human CSF3 as represented by the fragment Ala 30-Pro 207 of the full length protein. After this MBP-CSF3 fusion gene product the gene for the sulfhydryl oxidase Erv1p from *S. cerevisiae* has been cloned (Met 1-Glu 189) (SEQ ID NO: 5), with suitable ribosome binding sites to initiate translation of both; see FIG. 5. This polycistronic vector co-expresses MBP-CSF3 and Erv1p upon induction with IPTG.

pVD110 is a derivative of pVD109, in which the gene for the mature form of DsbC from *E. coli* (Asp 21-Lys 236) (SEQ ID NO: 10) has been cloned before the gene for MBP-CSF3 (with suitable ribosome binding sites to initiate translation of all; see FIG. 5). This polycistronic vector co-expresses MBP-CSF3, Erv1p and DsbC upon induction with IPTG.

pVD111 is a derivative of pVD109, in which the gene for the mature form of PDI from *H. sapiens* (Asp 18-Leu 508) (SEQ ID NO: 11) has been cloned before the gene for MBP-CSF3 (with suitable ribosome binding sites to initiate translation of all; see FIG. 5). This polycistronic vector co-expresses MBP-CSF3, Erv1p and PDI upon induction with IPTG.

pVD112 is a polycistronic derivative of pET23a which has a gene encoding for a cytoplasmically targeted MBP tag (as represented by the fragment Lys 27-Thr 392 plus a linker encoding the amino acid sequence NSSSNNNNHM (SEQ ID NO: 13) followed in frame with the mature form of mature human BMP4 as represented by the fragment Pro 294-Arg 408 of the full length protein. After this MBP-CSF3 fusion gene product the gene for the sulfhydryl oxidase Erv1p from *S. cerevisiae* has been cloned (Met 1-Glu 189), with suitable ribosome binding sites to initiate translation of both; see FIG. 5. This polycistronic vector co-expresses MBP-BMP4 and Erv1p upon induction with IPTG.

pVD114 is a derivative of pVD112, in which the gene for the mature form of DsbC from *E. coli* (Asp 21-Lys 236) (SEQ ID NO: 10) have been cloned before the gene for MBP-BMP4 (with suitable ribosome binding sites to initiate translation of all; see FIG. 5). This polycistronic vector co-expresses MBP-BMP4, Erv1p and DsbC upon induction with IPTG.

pVD113 is a derivative of pVD112, in which the gene for the mature form of PDI from *H. sapiens* (Asp 18-Leu 508) (SEQ ID NO: 11) have been cloned before the gene for MBP-BMP4 (with suitable ribosome binding sites to initiate translation of all; see FIG. 5). This polycistronic vector co-expresses MBP-BMP4, Erv1p and PDI upon induction with IPTG.

*E. coli* strains with these expression vectors were streaked out from glycerol stocks stored at −70° C. onto agar plates containing suitable antibiotics to allow for selection. The next day one colony from these plates were used to inoculate 5 mls of LB media, containing suitable antibiotics, and grown overnight at 30° C., 200 rpm. This overnight culture was used to seed a 50 mls culture of LB containing suitable antibiotics in a 250 ml flask to an optical density of 0.05 at 600 nm ($OD_{600}$). This culture was grown at 30° C., 200 rpm until the $OD_{600}$ reached 0.4 at which point protein production was induced by the addition of 1 mM IPTG. The cells were then grown for 4 hours at 30° C., 200 rpm and the final $OD_{600}$ measured. The cells were collected by centrifugation and resuspended to an $OD_{600}$ equivalent of 10 in 20 mM sodium phosphate pH 7.4, 20 µg/ml DNase, 0.1 mg/ml egg white lysozyme and frozen. Cells were lysed by freeze-thawing. Where appropriate, the insoluble fraction was removed by centrifugation and the soluble fraction removed quickly to a new container.

Figure 9:
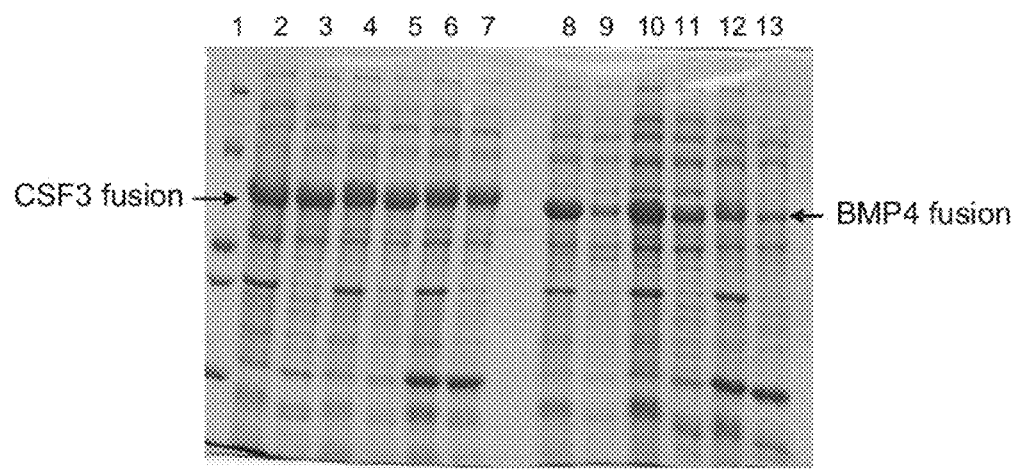
FIG. 9 shows SDS-PAGE from expression of the human CSF3 (lanes 2-7) and BMP4 (lanes 8-13) as fusion proteins with MBP in the cytoplasm of *E. coli* with co-expression with a sulfhydryl oxidase in LB media at 30° C. and co-expression of PDI (lanes 4, 5, 10, 11) or DsbC (lanes 6, 7, 12, 13). Even numbered lanes show the total *E. coli* lysates, odd numbered lanes show the soluble fractions (except lane 1 which shows molecular weight markers). The position of the MBP fusion proteins CSF3 and BMP4 are marked with arrows.

FIG. 9 shows SDS-PAGE from expression of the human CSF3 (lanes 2-7) and BMP4 (lanes 8-13) as fusion proteins with MBP in the cytoplasm of *E. coli* BL21 (DE3) pLysS with co-expression with a sulfhydryl oxidase in LB media at 30° C. and co-expression of PDI (lanes 4, 5, 10, 11) or DsbC (lanes 6, 7, 12, 13). Even numbered lanes show the total *E. coli* lysates, odd numbered lanes show the soluble fractions (except lane 1 which shows molecular weight markers). The position of the MBP fusion proteins CSF3 and BMP4 are marked with arrows. In *E. coli* BL21 (DE3) pLysS with no co-expression of a sulfhydryl oxidase no soluble protein expression can be observed for either protein but our system allows soluble expression of both.

The expression of CSF3 or BMP4 in the cytoplasm of *E. coli* BL21 (DE3) pLysS results in the formation of inclusion bodies. However, the expression of either protein in fusion with MBP along with co-expression of a sulfhydryl oxidase and the isomerase PDI or DsbC results in production of soluble protein (see FIG. 9).

Example 6

Efficient Production of Active Kringle tPA

Tissue plasminogen activator (tPA) is a protease that converts plasminogen to plasmin, the major enzyme involved in the breakdown of blood clots. It is used medically to treat pulmonary embolism, myocardial infarction and stroke. It is a large protein that contains 16 non-sequential and one sequential disulfide bond and in addition has one free thiol group in the native structure. It is available under the names Activase and Retavase. Retavase is a fragment of tPA which only contains the kringle 2 and protease domains. As such it contains only 9 disulfide bonds.

pKEHS1156, is a derivative of pET23a which has cloned into the multi-cloning site a gene encoding for an N-terminal hexa-histidine tag (MHHHHHHM) SEQ ID NO: 12 followed in frame with the form of Human tPA which contains the kringle 2 and protease domains as represented by the fragment Gly 211-Pro 562 of the full length protein. This vector expresses Kringle-tPA upon induction with IPTG.

pKEHS1165 is a derivative of pKEHS1156, in which the gene for the sulfhydryl oxidase Erv1p from S. cerevisiae has been cloned (Met 1-Glu 189) after the gene for Kringle-tPA (with suitable ribosome binding sites to initiate translation of both; see FIG. 5). This polycistronic vector co-expresses Kringle-tPA and Erv1p upon induction with IPTG.

pFH219 is a derivative of pKEHS1156, in which the gene for the sulfhydryl oxidase Erv1p from S. cerevisiae (Met 1-Glu 189) (SEQ ID NO: 5) and the gene for the mature form of DsbC from E. coli (Asp 21-Lys 236) (SEQ ID NO: 10) have been cloned after the gene for Kringle-tPA (with suitable ribosome binding sites to initiate translation of all; see FIG. 5). This polycistronic vector co-expresses Kringle-tPA, Erv1p and DsbC upon induction with IPTG.

pVD122 is a derivative of pET23a which has been cloned into the multi-cloning site a gene encoding for a cytoplasmically targeted N-terminal MBP tag (as represented by the fragment Lys 27-Thr 392 plus a linker encoding the amino acid sequence GSGSGSGSGSIEGRGSGSGSGSGSHM (SEQ ID NO: 14) followed in frame with the form of Human tPA which contains the kringle 2 and protease domains as represented by the fragment Gly 211-Pro 562 of the full length protein. This vector expresses the MBP-Kringle-tPA fusion protein upon induction with IPTG.

pVD163 is a derivative of pVD122, in which the gene for the sulfhydryl oxidase Erv1p from S. cerevisiae has been cloned (Met 1-Glu 189) after the gene for MBP-Kringle-tPA (with suitable ribosome binding sites to initiate translation of both; see FIG. 5). This polycistronic vector co-expresses MBP-Kringle-tPA and Erv1p upon induction with IPTG.

pVD171 is a derivative of pVD122, in which the gene for the mature form of DsbC from E. coli has been cloned (Asp 21-Lys 236) (SEQ ID NO: 10) after the gene for MBP-Kringle-tPA (with suitable ribosome binding sites to initiate translation of both; see FIG. 5). This polycistronic vector co-expresses MBP-Kringle-tPA and mature DsbC upon induction with IPTG.

pVD170 is a derivative of pVD122, in which the gene for the mature form of PDI from H. sapiens has been cloned (Asp 18-Leu 508) (SEQ ID NO: 11) after the gene for MBP-Kringle-tPA (with suitable ribosome binding sites to initiate translation of both; see FIG. 5). This polycistronic vector co-expresses MBP-Kringle-tPA and mature PDI upon induction with IPTG.

pVD164 is a derivative of pVD163, in which the gene for the mature form of DsbC from E. coli (Asp 21-Lys 236) (SEQ ID NO: 10) has been cloned after the genes for MBP-Kringle-tPA and Erv1p (with suitable ribosome binding sites to initiate translation of all; see FIG. 5). This polycistronic vector co-expresses MBP-Kringle-tPA, Erv1p and DsbC upon induction with IPTG.

pVD165 is a derivative of pVD163, in which the gene for the mature form of PDI from H. sapiens (Asp 18-Leu 508) (SEQ ID NO: 11) have been cloned after the genes for MBP-Kringle-tPA and Erv1p (with suitable ribosome binding sites to initiate translation of all; see FIG. 5). This polycistronic vector co-expresses MBP-Kringle-tPA, Erv1p and PDI upon induction with IPTG.

pFH256 is a derivative of pLysS in which the gene for sulfhydryl oxidase Erv1p from S. cerevisiae (Met 1-Glu 189) (SEQ ID NO: 5) and the gene for the mature form of PDI from H. sapiens (Asp 18-Leu 508) (SEQ ID NO: 11) have been cloned under an arabinose inducible promoter/terminator system. This vector allows pre-expression of Erv1p and PDI upon induction with arabinose.

pFH255 is a derivative of pLysS in which the gene for sulfhydryl oxidase Erv1p from S. cerevisiae (Met 1-Glu 189) (SEQ ID NO: 5) and the gene for the mature form of DsbC from E. coli (Asp 21-Lys 236) (SEQ ID NO: 10) have been cloned under an arabinose inducible promoter/terminator system. This vector allows pre-expression of Erv1p and DsbC upon induction with arabinose.

E. coli strains with these expression vectors (excluding strains which contain pFH255 or pFH256) were streaked out from glycerol stocks stored at −70° C. onto agar plates containing suitable antibiotics to allow for selection. The next day one colony from these plates were used to inoculate 5 mls of LB media, containing suitable antibiotics, and grown overnight at 30° C., 200 rpm. This overnight culture was used to seed a 50 mls culture of LB containing suitable antibiotics in a 250 ml flask to an optical density of 0.05 at 600 nm ($OD_{600}$). This culture was grown at 30° C., 200 rpm until the $OD_{600}$ reached 0.4 at which point protein production was induced by the addition of 1 mM IPTG. The cells were then grown for 4 hours at 30° C., 200 rpm and the final $OD_{600}$ measured. The cells were collected by centrifugation and resuspended to an $OD_{600}$ equivalent of 10 in 20 mM sodium phosphate pH 7.4, 20 μg/ml DNase, 0.1 mg/ml egg white lysozyme and frozen. Cells were lysed by freeze-thawing. Where appropriate, the insoluble fraction was removed by centrifugation and the soluble fraction removed quickly to a new container.

E. coli strains which contain pFH255 or pFH256 in addition to the expression vectors for derivatives of tPA were streaked out from glycerol stocks stored at −70° C. onto agar plates containing suitable antibiotics to allow for selection. The next day one colony from these plates were used to inoculate 5 mls of LB media, containing suitable antibiotics, and grown overnight at 30° C., 200 rpm. This overnight culture was used to seed a 50 mls culture of LB containing suitable antibiotics in a 250 ml flask to an optical density of 0.05 at 600 nm ($OD_{600}$). This culture was grown at 30° C., 200 rpm until the $OD_{600}$ reached 0.4 at which point pre-induction of Erv1p/PDI or Erv1p/PDI was induced by the addition of 0.5% arabinose. After 30 minutes production of the tPA derivatives was induced by the addition of 1 mM IPTG. The cells were then grown for 4 hours at 30° C., 200 rpm and the final $OD_{600}$ measured. The cells were collected by centrifugation and resuspended to an $OD_{600}$ equivalent of 10 in 20 mM sodium phosphate pH 7.4, 20 μg/ml DNase, 0.1 mg/ml egg white lysozyme and frozen. Cells were lysed by freeze-thawing. Where appropriate, the insoluble fraction was removed by centrifugation and the soluble fraction removed quickly to a new container.

Figure 10:
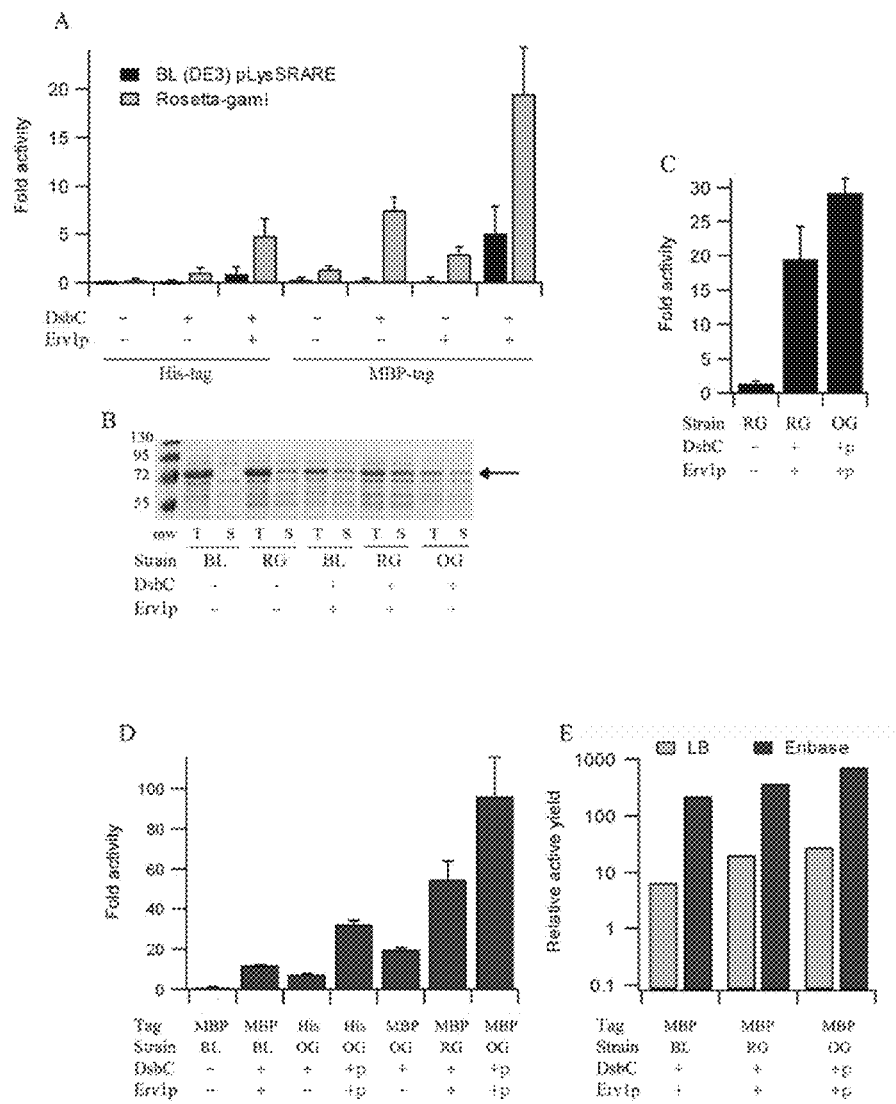
FIG. 10 shows analysis of human kringle tPA expressed in various systems in LB media at 30° C. Panel A) shows measurements for the activity of human kringle tPA with either an N-terminal His-tag or N-terminal MBP-tag expression in the cytoplasm of *E. coli*. BL21 pLysS RARE (BL) or rosetta-gami (RG) or origami (OG), with co-expression with the sulfhydryl oxidase Erv1p and/or DsbC. The data is normalized to the equivalent of the best previously reported system (a ΔtrxB Δgor strain with co-expression of mature DsbC) Panel B) SDS-PAGE from expression of the human kringle tPA as a fusion protein with MBP in the cytoplasm of *E. coli*. BL21 pLysS RARE (BL) or rosetta-gami (RG) or origami (OG), with co-expression with the sulfhydryl oxidase Erv1p and DsbC. Alternate lanes show the total *E. coli* lysates (T), and the soluble fractions (S). The position of the MBP-kringle tPA fusion protein is marked with an arrow. Panels C-E) show the results from measurements for the activity of the MBP-kringle t-PA fusion protein.

FIG. 10 shows analysis of human kringle tPA in various systems in LB media at 30° C. Activity measurements for the activity of hum an kringle tPA expressed in the cytoplasm of E. coli using the Roche chromogenic substrate for tPA. The intrinsic protease activity of the E. coli lysate has been subtracted. The human kringle tPA is expressed either as a protein with an N-terminal his tag or as a protein with an N-terminal MBP-tag. The data is normalized to the equivalent of the best previously reported system, a ΔtrxB Δgor strain with co-expression of mature DsbC. When present the sulfhydryl oxidase Erv1p and/or mature DsbC are co-expressed from a polycistronic vector. Panel B). Panel A) SDS-PAGE from expression of the human kringle tPA as a fusion protein with MBP in the cytoplasm of E. coli. BL21 pLysS RARE (BL) or rosetta-gami (RG), with and without co-expression with the sulfhydryl oxidase Erv1p and DsbC. Lanes marked with (T) and (S) show the total E. coli lysates and the soluble fractions, respectively. The position of the MBP-kringle tPA fusion protein is marked with an arrow. There is a clear correlation between soluble expression of soluble fusion protein and activity. Panels C-E) Activity measurements for the activity of human kringle tPA expressed in the cytoplasm of E. coli using the Roche chromogenic substrate for tPA. The human kringle tPA is expressed either as a protein with an N-terminal his tag or as a protein with an N-terminal MBP-tag. The data is normalized to the equivalent of the best previously reported system, a ΔtrxB Δgor strain with co-expression of mature DsbC. Panel C) shows the effects of co- vs pre-expression of the sulfhydryl oxidase Erv1p and mature DsbC. The strains used were BL21 pLysS RARE (BL) or rosetta-gami (RG) or origami (OG) with co-expression (+) or pre-expression (+p) for 30 minutes of the sulfhydryl oxidase Erv1p and mature DsbC. Note the increase in activity with pre-expression comes despite the significant reduction in expression levels (see panel B) in origami compared with rosetta-gami due to the expression of rare tRNAs in the later. Panel D) Relative activity of human kringle tPA produced in EnBase media (Biosilta Oy) at 30° C. Panel E) Relative yields of active protein produced in LB and EnBase media.

Expression of tPA or kringle tPA (similar but not identical to Retavase) in the cytoplasm of E. coli resulted in the production of insoluble inclusion bodies. Co-expression of a sulfhydryl oxidase increased the activity of kringle tPA significantly (see FIG. 10). Combining this with co-expression of an isomerase, DsbC and/or with expressing kringle tPA as a fusion protein with Maltose binding protein (MBP) or using the rosetta-gami or origami strains further increased the level of active protein produced (see FIG. 10) and the amount of soluble protein produced (see FIG. 10).

Example 7

Efficient Production of Soluble Folded BPTI and Disulfide Mutants Therein

Bovine pancreatic trypsin inhibitor (BPTI) is a low molecular weight inhibitor of trypsin, kallikrein, chymotrypsin and plasmin. It is available under the name Trasylol and is used to inhibit coagulation during bypass surgery. It is a small protein which contains three non-sequential disulfide bonds. The folding intermediates of BPTI are of academic interest to understand protein folding pathways and especially the roles of protein folding catalysts in these processes.

pHEE12, is a derivative of pET23a which has cloned into the multi-cloning site a gene encoding for an N-terminal hexa-histidine tag (MHHHHHM) SEQ ID NO: 12, followed in frame with the mature form of Bovine pancreatic trypsin inhibitor (BPTI) as represented by the fragment Arg 36-Ala 93 of the full length protein. This vector expresses BPTI upon induction with IPTG.

pHEE8, is a derivative of pHEE12 in which Cysteine 49 and Cysteine 73 have been mutated to Alanine. This vector expresses C49A/C73A BPTI upon induction with IPTG.

pHEE10, is a derivative of pHEE12 in which Cysteine 65 and Cysteine 86 have been mutated to Alanine. This vector expresses C65A/C86A BPTI upon induction with IPTG.

pKEHS1208 is a derivative of pLysS in which the gene for sulfhydryl oxidase Erv1p from S. cerevisiae (Met 1-Glu 189) (SEQ ID NO: 5) and the gene for the mature form of PDI from H. sapiens (Asp 18-Leu 508) (SEQ ID NO: 11) have been cloned under an arabinose inducible promoter/terminator system. This vector allows pre-expression of Erv1p and PDI upon induction with arabinose.

pKEHS1209 is a derivative of pLysS in which the gene for sulfhydryl oxidase Erv1p from S. cerevisiae (Met 1-Glu 189) (SEQ ID NO: 5) and the gene for the mature form of DsbC from E. coli (Asp 21-Lys 236) (SEQ ID NO: 10) have been cloned under an arabinose inducible promoter/terminator system. This vector allows pre-expression of Erv1p and DsbC upon induction with arabinose.

E. coli strains with these expression vectors (excluding strains which contain pKEHS1208 or pKEHS1209) were streaked out from glycerol stocks stored at −70° C. onto agar plates containing suitable antibiotics to allow for selection. The next day one colony from these plates were used to inoculate 5 mls of LB media, containing suitable antibiotics, and grown overnight at 30° C., 200 rpm. This overnight culture was used to seed a 50 mls culture of LB containing suitable antibiotics in a 250 ml flask to an optical density of 0.05 at 600 nm ($OD_{600}$). This culture was grown at 30° C., 200 rpm until the $OD_{600}$ reached 0.4 at which point protein production was induced by the addition of 1 mM IPTG. The cells were then grown for 4 hours at 30° C., 200 rpm and the final $OD_{600}$ measured. The cells were collected by centrifugation and resuspended to an $OD_{600}$ equivalent of 10 in 20 mM sodium phosphate pH 7.4, 20 µg/ml DNase, 0.1 mg/ml egg white lysozyme and frozen. Cells were lysed by freeze-thawing. Where appropriate, the insoluble fraction was removed by centrifugation and the soluble fraction removed quickly to a new container.

E. coli strains which contain pKEHS1208 or pKEHS1209 in addition to the expression vectors for derivatives of BPTI were streaked out from glycerol stocks stored at −70° C. onto agar plates containing suitable antibiotics to allow for selection. The next day one colony from these plates were used to inoculate 5 mls of LB media, containing suitable antibiotics, and grown overnight at 30° C., 200 rpm. This overnight culture was used to seed a 50 mls culture of LB containing suitable antibiotics in a 250 ml flask to an optical density of 0.05 at 600 nm ($OD_{600}$). This culture was grown at 30° C., 200 rpm until the $OD_{600}$ reached 0.4 at which point pre-induction of Erv1p/PDI or Erv1p/DsbC was induced by the addition of 0.5% arabinose. After 30 minutes production of the BPTI derivatives was induced by the addition of 1 mM IPTG. The cells were then grown for 4 hours at 30° C., 200 rpm and the final $OD_{600}$ measured. The cells were collected by centrifugation and resuspended to an $OD_{600}$ equivalent of 10 in 20 mM sodium phosphate pH 7.4, 20 µg/ml DNase, 0.1 mg/ml egg white lysozyme and frozen. Cells were lysed by freeze-thawing. Where appropriate, the insoluble fraction was removed by centrifugation and the soluble fraction removed quickly to a new container.

Figure 11:
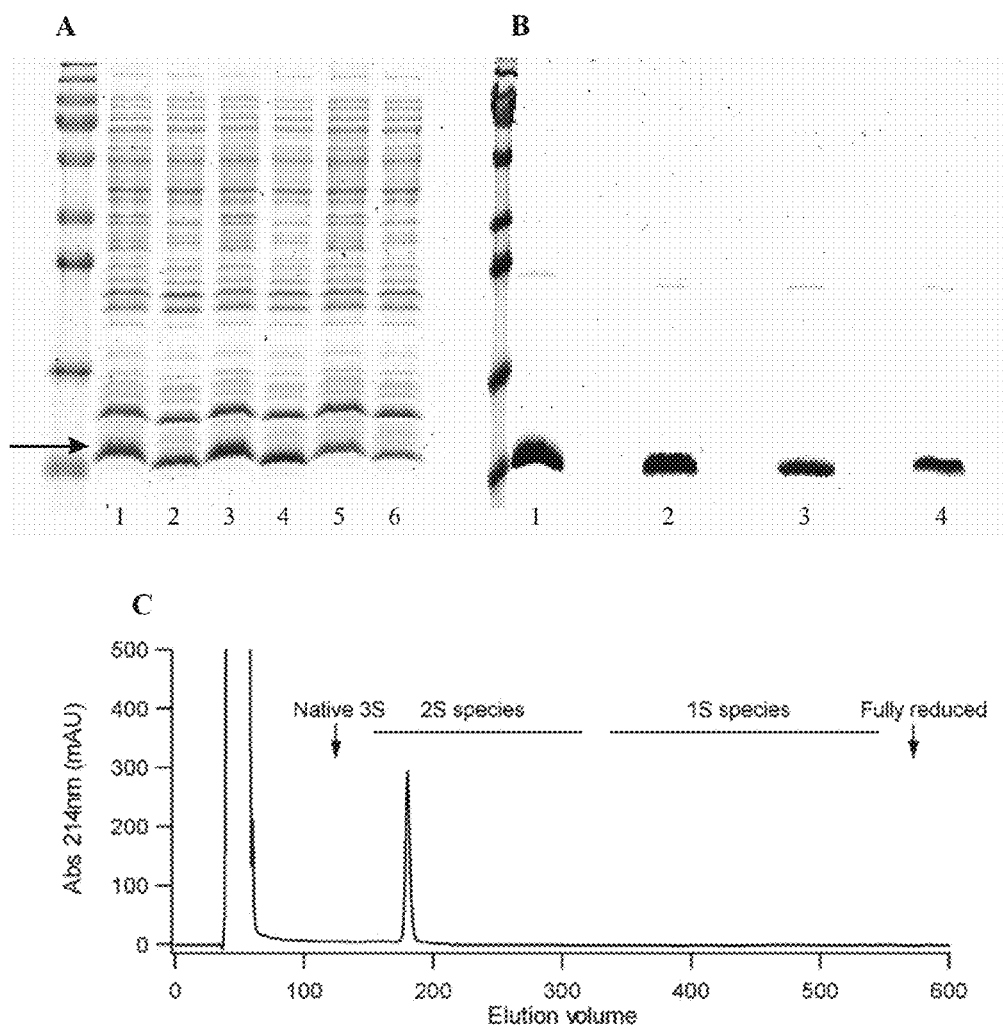
FIG. 11 shows analysis of BPTI production in origami+ pre-expression of the sulfhydryl oxidase and PDI in LB media at 30° C. Panel A) SDS-PAGE from expression of BPTI wild type (lanes 1 and 2), along with the C49A/C73A (lanes 3 and 4) and C65A/C86A (lanes 5 and 6) mutants, which should contain only 2 disulfide bonds, in the cytoplasm of origami *E. coli* with pre-expression of the sulfhydryl oxidase (SO) and PDI. Odd numbered lanes show the total *E. coli* lysates, even numbered lanes show the soluble fractions. The position of BPTI is marked with an arrow. Panel B) Purification of the C49A/C73A or C65A/C86A mutants of BPTI using immobilized metal affinity chromatography and subsequent analysis by reducing (lanes 1 and 3) and non-reducing (lanes 2 and 4) SDS-PAGE indicated that only monomeric species were obtained for the C49A/C73A (lanes 1 and 2) and for the C65A/C86A (lanes 3 and 4) BPTI mutants i.e. no mixed disulfides were formed. Panel C) Analysis of the C49A/C73A mutants using immobilized metal affinity chromatography and subsequent analysis by reverse phase HPLC analysis. The elution positions of the native species containing 3 disulfides, the fully reduced species and the intermediate species containing only 1 or 2 disulfides are indicated. These results indicate that only a single two disulfide species is obtained.

When N-terminally hexa-histidine tagged wild-type mature BPTI or the C49A/C73A or C65A/C86A mutants, which mimic two of the two disulfide bond containing intermediates, are expressed in the cytoplasm of E. coli they form inclusion bodies. In contrast, when they are co-expressed with a sulfhydryl oxidase and a thiol-disulfide isomerase soluble protein is formed (see FIG. 11). Purification of the C49A/C73A or C65A/C86A mutants using immobilized metal affinity chromatography and subsequent analysis by reverse phase HPLC indicated that the purified proteins were homogenous, with the elution point being equivalent to the relevant two disulfide containing wild-type folding intermediate (see FIG. 11) i.e. only a single disulfide bond containing species which contained the correct disulfides was obtained.

Example 8

Efficient Production of Soluble Interferon α2 and Interleukin 17

Interferon α2 is an anti-viral protein produced by macrophages. It contains 2 non-sequential disulfide bonds. Interleukin 17 is a cytokine that induces the production of proinflammatory cytokines. It contains 2 non-sequential disulfide bonds.

pGZ10 is a derivative of pET23a which has cloned into the multi-cloning site a gene encoding for an N-terminal hexa-histidine tag (MHHHHHHM) (SEQ ID NO: 12) followed in frame with the mature form of human interferon α2 as represented by the fragment Cys 24-Glu 188 of the full length protein. This vector expresses interferon α2 upon induction with IPTG.

pGZ15 is a derivative of pET23a which has cloned into the multi-cloning site a gene encoding for a cytoplasmically targeted N-terminal MBP tag (as represented by the fragment Lys 27-Thr 392 plus a linker encoding the amino acid sequence GSGSGSGSGSIEGRGSGSGSGSGSHM) (SEQ ID NO: 14) followed in frame with the mature form of human interferon α2 as represented by the fragment Cys 24-Glu 188 of the full length protein. This vector expresses the MBP-interferon α2 fusion protein upon induction with IPTG.

pMHR5 is a derivative of pET23a which has cloned into the multi-cloning site a gene encoding for a cytoplasmically targeted N-terminal MBP tag (as represented by the fragment Lys 27-Thr 392 plus a linker encoding the amino acid sequence GSGSGSGSGSIEGRGSGSGSGSGSHM) (SEQ ID NO: 14) followed in frame with the mature form of human interleukin 17 as represented by the fragment Gly 24-Ala 155 of the full length protein. This vector expresses the MBP-interleukin 17 fusion protein upon induction with IPTG.

pFH255 is a derivative of pLysS in which the gene for sulfhydryl oxidase Erv1p from *S. cerevisiae* (Met 1-Glu 189) and the gene for the mature form of DsbC from *E. coli* (Asp 21-Lys 236) have been cloned under an arabinose inducible promoter/terminator system. This vector allows pre-expression of Erv1p and DsbC upon induction with arabinose.

*E. coli* strains which contain pFH255 in addition to the expression vectors for derivatives of interferon α2 or interleukin 17 were streaked out from glycerol stocks stored at −70° C. onto agar plates containing suitable antibiotics to allow for selection. The next day one colony from these plates were used to inoculate 5 mls of LB media, containing suitable antibiotics, and grown overnight at 30° C., 200 rpm. This overnight culture was used to seed a 50 mls culture of LB containing suitable antibiotics in a 250 ml flask to an optical density of 0.05 at 600 nm ($OD_{600}$). This culture was grown at 30° C., 200 rpm until the $OD_{600}$ reached 0.4 at which point pre-induction of Erv1p/PDI or Erv1p/DsbC was induced by the addition of 0.5% arabinose. After 30 minutes production of the BPTI derivatives was induced by the addition of 0.5 mM IPTG. The cells were then grown for 4 hours at 30° C., 200 rpm and the final $OD_{600}$ measured. The cells were collected by centrifugation and resuspended to an $OD_{600}$ equivalent of 10 in 20 mM sodium phosphate pH 7.4, 20 μg/ml DNase, 0.1 mg/ml egg white lysozyme and frozen. Cells were lysed by freeze-thawing. Where appropriate, the insoluble fraction was removed by centrifugation and the soluble fraction removed quickly to a new container.

Figure 12:
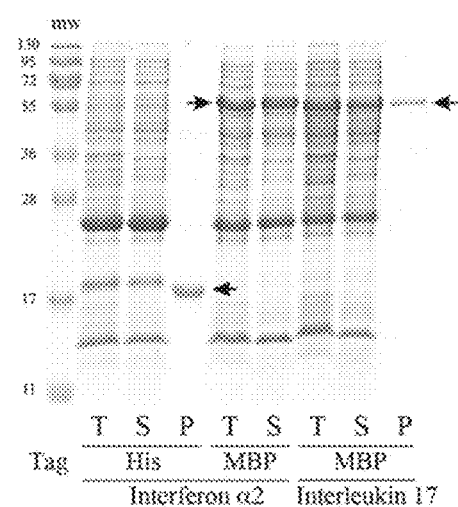
FIG. 12 shows analysis of the production of human interferon α2 and interleukin 17 in *E. coli* with co- or pre-expression of a sulfhydryl oxidase.

FIG. 12 shows SDS-PAGE analysis of production of interferon α2 and interleukin 17 in the cytoplasm of the *E. coli* strain origami in EnBase media at 30° C. Lanes show total (T) and soluble (S) fractions of the *E. coli* lysates or protein purified (P) using an NTA-spin column or amylose column (P). The positions of the interferon α2 and interleukin 17 fusion proteins are marked with arrows.

When N-terminally hexa-histidine or MBP-tagged mature interferon α2 or MBP-tagged interleukin 17 are expressed in the cytoplasm of *E. coli* they form inclusion bodies. In contrast, when there is pre-expression of a sulfhydryl oxidase and mature DsbC in the origami strain of *E. coli* soluble protein is obtained (see FIG. 12). All three can be purified to homogeneity by appropriate affinity chromatography.

Example 9

Efficient Production of Soluble Disulfide Linked Resistin

Resistin is a hormone linked to suppression of glucose uptake into adipose cells by insulin. The mature protein contains 5 non-sequential disulfide bonds and an intermolecular disulfide which links two resistin monomers to together to form a disulfide linked homodimer.

pGZ16, is a derivative of pET23a which has cloned into the multi-cloning site a gene encoding for a cytoplasmically targeted N-terminal MBP tag (as represented by the fragment Lys 27-Thr 392 plus a linker encoding the amino acid sequence GSGSGSGSGSIEGRGSGSGSGSGSHM) (SEQ ID NO:14) followed in frame with the mature form of human resistin as represented by the fragment Lys 19-Pro 108 of the full length protein. This vector expresses the MBP-resistin fusion protein upon induction with IPTG. The fusion protein can be cleaved in the linker region by factor Xa.

pFH255 is a derivative of pLysS in which the gene for sulfhydryl oxidase Erv1p from *S. cerevisiae* (Met 1-Glu 189) and the gene for the mature form of DsbC from *E. coli* (Asp 21-Lys 236) have been cloned under an arabinose inducible promoter/terminator system. This vector allows pre-expression of Erv1p and DsbC upon induction with arabinose.

*E. coli* strains with these expression vectors (excluding strains which contain pKEHS1208 or pKEHS1209) were streaked out from glycerol stocks stored at −70° C. onto agar plates containing suitable antibiotics to allow for selection. The next day one colony from these plates were used to inoculate 5 mls of LB media, containing suitable antibiotics, and grown overnight at 30° C., 200 rpm. This overnight culture was used to seed a 50 mls culture of LB containing suitable antibiotics in a 250 ml flask to an optical density of 0.05 at 600 nm ($OD_{600}$). This culture was grown at 30° C., 200 rpm until the $OD_{600}$ reached 0.4 at which point protein production was induced by the addition of 0.5 mM IPTG. The cells were then grown for 4 hours at 30° C., 200 rpm and the final $OD_{600}$ measured. The cells were collected by centrifugation and resuspended to an $OD_{600}$ equivalent of 10 in 20 mM sodium phosphate pH 7.4, 20 μg/ml DNase, 0.1 mg/ml egg white lysozyme and frozen. Cells were lysed by freeze-thawing. Where appropriate, the insoluble fraction was removed by centrifugation and the soluble fraction removed quickly to a new container.

E. coli strains which contain pFH255 in addition to the expression vectors for derivatives of resistin were streaked out from glycerol stocks stored at −70° C. onto agar plates containing suitable antibiotics to allow for selection. The next day one colony from these plates were used to inoculate 5 mls of LB media, containing suitable antibiotics, and grown overnight at 30° C., 200 rpm. This overnight culture was used to seed a 50 mls culture of LB containing suitable antibiotics in a 250 ml flask to an optical density of 0.05 at 600 nm ($OD_{600}$). This culture was grown at 30° C., 200 rpm until the $OD_{600}$ reached 0.4 at which point pre-induction of Erv1p/PDI or Erv1p/DsbC was induced by the addition of 0.5% arabinose. After 30 minutes production of the BPTI derivatives was induced by the addition of 0.5 mM IPTG. The cells were then grown for 4 hours at 30° C., 200 rpm and the final $OD_{600}$ measured. The cells were collected by centrifugation and resuspended to an $OD_{600}$ equivalent of 10 in 20 mM sodium phosphate pH 7.4, 20 µg/ml DNase, 0.1 mg/ml egg white lysozyme and frozen. Cells were lysed by freeze-thawing. Where appropriate, the insoluble fraction was removed by centrifugation and the soluble fraction removed quickly to a new container.

Figure 13:
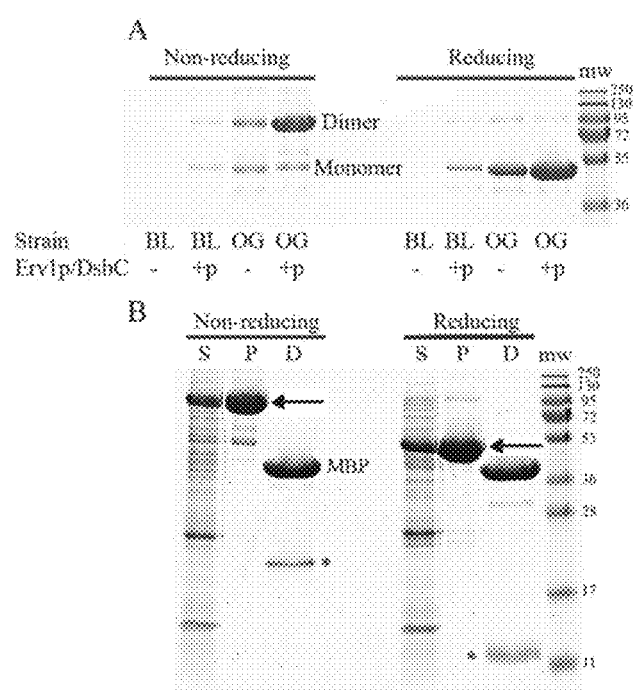
FIG. 13 shows analysis of resistin expressed in the cytoplasm of *E. coli* with or without the pre-expression of a sulfhydryl oxidase and DsbC. Panel A) SDS-PAGE analysis of purified MBP-resistin under reducing and non-reducing conditions. Panel B) SDS-PAGE analysis of mature resistin produced in origami with pre-expression of a sulfhydryl oxidase and DsbC.

FIG. 13 shows SDS-PAGE analysis of production of resistin in the cytoplasm of the E. coli strains in LB media at 30° C. Panel A) Analysis, under non-reducing and reducing conditions, of MBP-resistin fusion protein purified using an amylose resin column, indicates that the production of the disulfide linked resistin dimer increase with pre-expression of the sulfhydryl oxidase Erv1p and mature DsbC in both wild-type and ΔtrxB Δgor strains. The strains used were BL21 pLysS RARE (BL) or origami (OG) with or without or pre-expression (+p) for 30 minutes of the sulfhydryl oxidase Erv1p and mature DsbC. Panel B) Analysis, under non-reducing and reducing conditions, of MBP-resistin fusion protein purified using an amylose resin column of protein produced in origami with pre-expression of the sulfhydryl oxidase Erv1p and mature DsbC. The lanes show soluble (S) fractions of the E. coli lysate, protein purified (P) using an amylose resin column and purified material that has been digested with Factor Xa (D) to release MBP and resistin. Resistin is marked with an * in the digested fraction lanes. The position of the MBP-resistin fusion is indicated with an arrow.

Our invention allows efficient production of disulfide linked homodimers of resistin.

Example 10

Efficient Production of $^{15}$N Labeled Human Growth Hormone 1 and Interleukin 6

Human growth hormone 1 (also known as somatotropin) plays a key role in growth control. It contains 2 sequential disulfide bonds. Interleukin 6 is a cytokine with a wide variety of biological responses including differentiation of B-cells, lymphocytes and monocytes. It contains 2 sequential disulfide bonds.

pHIA487, is a derivative of pET23a which has cloned into the multi-cloning site a gene encoding for an N-terminal hexa-histidine tag (MHHHHHHM) (SEQ ID NO: 12) followed in frame with the mature form of human growth hormone 1 as represented by the fragment Phe 27-Phe 217 of the full length protein. After this gene the gene for the sulfhydryl oxidase Erv1p from S. cerevisiae has been cloned (Met 1-Glu 189) which has been codon optimized for expression in E. coli (with suitable ribosome binding sites to initiate translation of both genes; see FIG. 5). This polycistronic vector co-expresses hexahistidine tagged human growth hormone and codon optimized Erv1p upon induction with IPTG.

pYOE8 is a derivative of pET23a which has cloned into the multi-cloning site a gene encoding for an N-terminal hexa-histidine tag (MHHHHHHM) (SEQ ID NO:12) followed in frame with the mature form of interleukin 6 as represented by the fragment Val30-Met212 of the full length protein. After this gene the gene for the sulfhydryl oxidase Erv1p from S. cerevisiae has been cloned (Met 1-Glu 189) which has been codon optimized for expression in E. coli (with suitable ribosome binding sites to initiate translation of both genes; see FIG. 5). This polycistronic vector co-expresses hexahistidine tagged interleukin 6 and codon optimized Erv1p upon induction with IPTG.

BL21 (DE3) pLysS E. coli strains with these co-expression vectors were streaked out from glycerol stocks stored at −70° C. onto agar plates containing suitable antibiotics to allow for selection. The next day one colony from these plates were used to inoculate 20 mls of $^{15}$N-labelled M9 minimal media, containing suitable antibiotics, and grown overnight at 30° C., 200 rpm. This overnight culture was used to seed a 400 mls culture of $^{15}$N-labelled M9 minimal media containing suitable antibiotics in a 2 L flask to an optical density of 0.1 at 600 nm ($OD_{600}$). This culture was grown at 30° C., 200 rpm until the $OD_{600}$ reached 0.4 at which point protein production was induced by the addition of 0.5 mM IPTG. The cells were then grown for 4 hours at 30° C., 200 rpm and the final $OD_{600}$ measured. The cells were collected by centrifugation and resuspended to an $OD_{600}$ equivalent of 10 in 20 mM sodium phosphate pH 7.4, 20 µg/ml DNase, 0.1 mg/ml egg white lysozyme and frozen. Cells were lysed by freeze-thawing. Where appropriate, the insoluble fraction was removed by centrifugation and the soluble fraction removed quickly to a new container.

Figure 14:
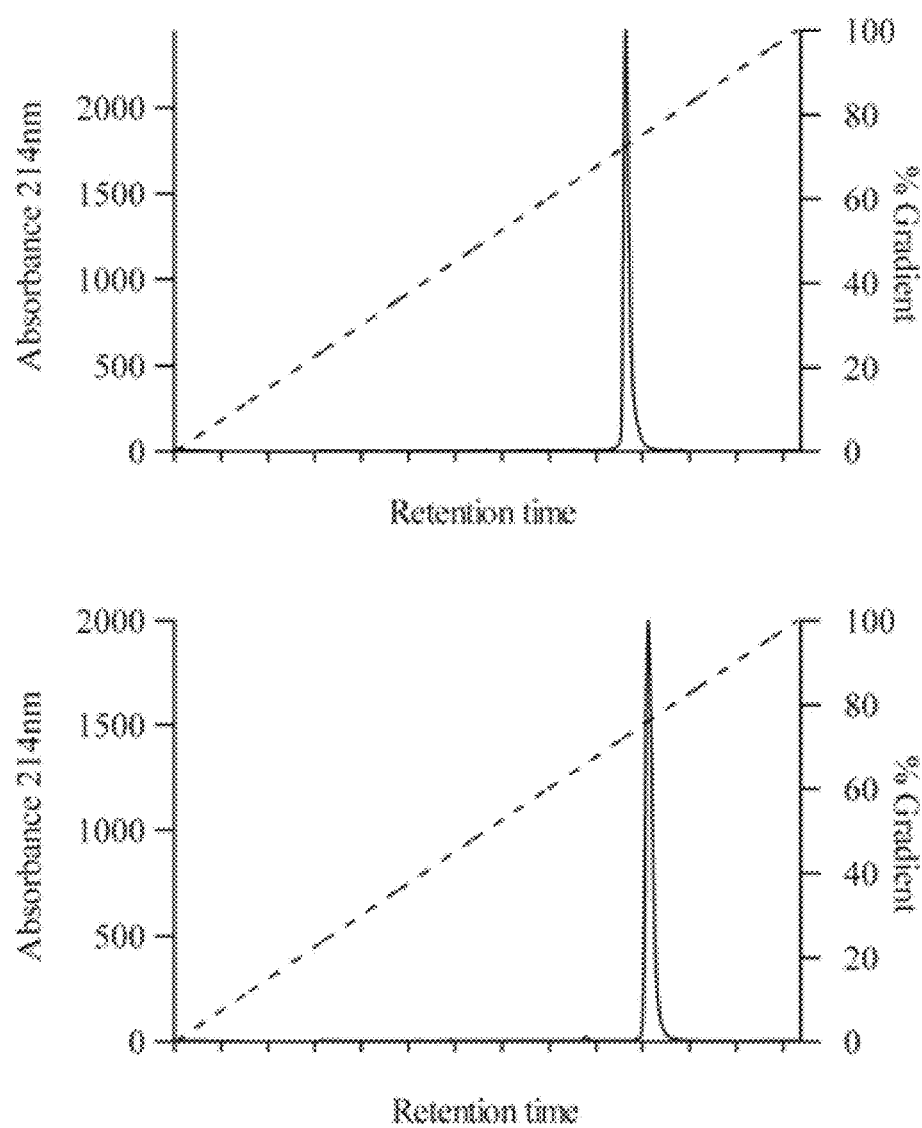
FIG. 14 shows reverse phase HPLC analysis of $^{15}N$ labeled interleukin 6 and human growth hormone 1 produced in $^{15}N$-labelled M9 minimal media with co-expression of a sulfhydryl oxidase.

Purification of $^{15}$N-labelled human growth hormone 1 and interleukin 6 using immobilized metal affinity chromatography and subsequent analysis by reverse phase HPLC indicated that the purified proteins were homogenous (see FIG. 14; upper panel interleukin 6, lower panel human growth hormone 1) i.e. only a single disulfide bond containing species was obtained. Parallel analysis by mass spectrometry and an Elman's assay for free thiol groups under native and denaturing conditions showed that >98% of $^{15}$N-labelled was achieved for both proteins and that there were no detectable free thiols i.e. that two disulfide bonds were formed in both proteins.

Our invention allows efficient production of disulfide containing human growth hormone and interleukin 6 from cytoplasmic expression in $^{15}$N-labelled minimal media. Parallel expression showed similar production of disulfide bonded proteins in LB and EnBase media.

The invention claimed is:

1. A prokaryotic host cell comprising one or more expression vectors encoding a cytoplasmically expressing sulfhydryl oxidase catalyzing a reaction: dithiol+$O_2$→2disulfides+2$H_2O$, and a cytoplasmically expressing eukaryotic or prokaryotic protein of interest containing one or more disulfide bonds wherein the protein of interest is produced in a soluble form and containing natively folded disulfide bonds in the cytoplasm of said prokaryotic host cell due to presence of the sulfhydryl oxidase in the cytoplasm.

2. The host cell according to claim 1, wherein the sulfhydryl oxidase uses FAD as a cofactor and contains one or more redox active disulfide bonds.

3. The host cell according to claim 1, wherein the sulfhydryl oxidase belongs to sulfhydryl oxidases comprising ERV/ALR sulfhydryl oxidase domain.

4. The host cell according to claim 2, wherein the sulfhydryl oxidase belongs to ERO family of sulfhydryl oxidases.

5. The host cell according to claim 1, wherein the prokaryotic host is a gram negative bacterium.

6. The host cell according to claim 1, wherein the host cell further expresses a thiol-disulfide isomerase in the cytoplasm.

7. The host cell according to claim 6, wherein the disulfide isomerase is PDI, or DsbC.

8. The host cell according to claim 6, wherein the sulfhydryl oxidase and the disulfide isomerase are induced separately or together with the protein of interest.

9. The host cell according to claim 1, wherein the host cell is deficient of thioredoxin reductase or glutathione reductase activity, or of both.

10. A vector system for a cytoplasmic expression in a prokaryotic host cell of a recombinant eukaryotic or prokaryotic protein of interest in a soluble form containing natively folded disulfide bonds, said vector system comprising:

a vector comprising a nucleotide sequence or having a site for the nucleotide sequence encoding a eukaryotic or a prokaryotic cytoplasmically expressing protein of interest said protein containing one or more disulfide bonds, and a nucleotide sequence encoding cytoplasmically expressing sulfhydryl oxidase catalyzing reaction dithiol+$O_2$→2 disulfides+2 $H_2O$ for folding the disulfide bonds for production of the eukaryotic or prokaryotic cytoplasmically expressing protein of interest in soluble form containing natively folded disulfide bonds, or a first vector comprising a nucleotide sequence encoding a eukaryotic or a prokaryotic cytoplasmically expressing protein of interest, or having a site for a nucleic acid sequence encoding a eukaryotic or a prokaryotic cytoplasmically expressing protein of interest, and a second vector comprising a nucleotide sequence encoding a cytoplasmically expressing sulfhydryl oxidase catalyzing reaction dithiol+$O_2$→2 disulfides+2 $H_2O$, for folding the disulfide bonds for production of the eukaryotic or prokaryotic cytoplasmically expressing protein of interest in soluble form containing natively folded disulfide bonds, and regulatory regions for multiplying and expressing said nucleotide sequences in a prokaryotic host cell.

11. The vector system according to claim 10, wherein the system further comprises a nucleotide sequence encoding a thiol-disulfide isomerase, said nucleotide sequence being in the same or in a different vector as the vectors in the vector system.

12. The vector system according to claim 11, wherein the sulfhydryl oxidase and thiol-disulfide isomerase are induced separately or together with the protein of interest.

13. A prokaryotic host cell, which comprises the vector system according to claim 10.

* * * * *

SEQUENCE LISTING

<160> NUMBER OF SEQ ID NOS: 14

<210> SEQ ID NO 1
<211> LENGTH: 563
<212> TYPE: PRT
<213> ORGANISM: Saccharomyces cerevisiae

<400> SEQUENCE: 1

```
Met Arg Leu Arg Thr Ala Ile Ala Thr Leu Cys Leu Thr Ala Phe Thr
 1               5                  10                  15

Ser Ala Thr Ser Asn Asn Ser Tyr Ile Ala Thr Asp Gln Thr Gln Asn
            20                  25                  30

Ala Phe Asn Asp Thr His Phe Cys Lys Val Asp Arg Asn Asp His Val
        35                  40                  45

Ser Pro Ser Cys Asn Val Thr Phe Asn Glu Leu Asn Ala Ile Asn Glu
    50                  55                  60

Asn Ile Arg Asp Asp Leu Ser Ala Leu Leu Lys Ser Asp Phe Lys
65                  70                  75                  80

Tyr Phe Arg Leu Asp Leu Tyr Lys Gln Cys Ser Phe Trp Asp Ala Asn
                85                  90                  95

Asp Gly Leu Cys Leu Asn Arg Ala Cys Ser Val Asp Val Val Glu Asp
            100                 105                 110

Trp Asp Thr Leu Pro Glu Tyr Trp Gln Pro Glu Ile Leu Gly Ser Phe
        115                 120                 125

Asn Asn Asp Thr Met Lys Glu Ala Asp Asp Ser Asp Asp Glu Cys Lys
    130                 135                 140

Phe Leu Asp Gln Leu Cys Gln Thr Ser Lys Lys Pro Val Asp Ile Glu
145                 150                 155                 160

Asp Thr Ile Asn Tyr Cys Asp Val Asn Asp Phe Asn Gly Lys Asn Ala
                165                 170                 175

Val Leu Ile Asp Leu Thr Ala Asn Pro Glu Arg Phe Thr Gly Tyr Gly
            180                 185                 190

Gly Lys Gln Ala Gly Gln Ile Trp Ser Thr Ile Tyr Gln Asp Asn Cys
        195                 200                 205

Phe Thr Ile Gly Glu Thr Gly Glu Ser Leu Ala Lys Asp Ala Phe Tyr
    210                 215                 220

Arg Leu Val Ser Gly Phe His Ala Ser Ile Gly Thr His Leu Ser Lys
225                 230                 235                 240

Glu Tyr Leu Asn Thr Lys Thr Gly Lys Trp Glu Pro Asn Leu Asp Leu
                245                 250                 255

Phe Met Ala Arg Ile Gly Asn Phe Pro Asp Arg Val Thr Asn Met Tyr
            260                 265                 270

Phe Asn Tyr Ala Val Val Ala Lys Ala Leu Trp Lys Ile Gln Pro Tyr
        275                 280                 285

Leu Pro Glu Phe Ser Phe Cys Asp Leu Val Asn Lys Glu Ile Lys Asn
    290                 295                 300

Lys Met Asp Asn Val Ile Ser Gln Leu Asp Thr Lys Ile Phe Asn Glu
305                 310                 315                 320

Asp Leu Val Phe Ala Asn Asp Leu Ser Leu Thr Leu Lys Asp Glu Phe
                325                 330                 335

Arg Ser Arg Phe Lys Asn Val Thr Lys Ile Met Asp Cys Val Gln Cys
            340                 345                 350

Asp Arg Cys Arg Leu Trp Gly Lys Ile Gln Thr Thr Gly Tyr Ala Thr
        355                 360                 365
```

-continued

```
Ala Leu Lys Ile Leu Phe Glu Ile Asn Asp Ala Asp Glu Phe Thr Lys
370                 375                 380
Gln His Ile Val Gly Lys Leu Thr Lys Tyr Glu Leu Ile Ala Leu Leu
385                 390                 395                 400
Gln Thr Phe Gly Arg Leu Ser Glu Ser Ile Glu Ser Val Asn Met Phe
                405                 410                 415
Glu Lys Met Tyr Gly Lys Arg Leu Asn Gly Ser Glu Asn Arg Leu Ser
            420                 425                 430
Ser Phe Phe Gln Asn Asn Phe Asn Ile Leu Lys Glu Ala Gly Lys
        435                 440                 445
Ser Ile Arg Tyr Thr Ile Glu Asn Ile Asn Ser Thr Lys Glu Gly Lys
    450                 455                 460
Lys Lys Thr Asn Asn Ser Gln Ser His Val Phe Asp Asp Leu Lys Met
465                 470                 475                 480
Pro Lys Ala Glu Ile Val Pro Arg Pro Ser Asn Gly Thr Val Asn Lys
                485                 490                 495
Trp Lys Lys Ala Trp Asn Thr Glu Val Asn Asn Val Leu Glu Ala Phe
            500                 505                 510
Arg Phe Ile Tyr Arg Ser Tyr Leu Asp Leu Pro Arg Asn Ile Trp Glu
        515                 520                 525
Leu Ser Leu Met Lys Val Tyr Lys Phe Trp Asn Lys Phe Ile Gly Val
    530                 535                 540
Ala Asp Tyr Val Ser Glu Thr Arg Glu Pro Ile Ser Tyr Lys Leu
545                 550                 555                 560
Asp Ile Gln

<210> SEQ ID NO 2
<211> LENGTH: 468
<212> TYPE: PRT
<213> ORGANISM: Homo sapiens

<400> SEQUENCE: 2

Met Gly Arg Gly Trp Gly Phe Leu Phe Gly Leu Leu Gly Ala Val Trp
1               5                   10                  15
Leu Leu Ser Ser Gly His Gly Glu Glu Gln Pro Pro Glu Thr Ala Ala
                20                  25                  30
Gln Arg Cys Phe Cys Gln Val Ser Gly Tyr Leu Asp Asp Cys Thr Cys
            35                  40                  45
Asp Val Glu Thr Ile Asp Arg Phe Asn Asn Tyr Arg Leu Phe Pro Arg
        50                  55                  60
Leu Gln Lys Leu Leu Glu Ser Asp Tyr Phe Arg Tyr Tyr Lys Val Asn
65                  70                  75                  80
Leu Lys Arg Pro Cys Pro Phe Trp Asn Asp Ile Ser Gln Cys Gly Arg
                85                  90                  95
Arg Asp Cys Ala Val Lys Pro Cys Gln Ser Asp Glu Val Pro Asp Gly
            100                 105                 110
Ile Lys Ser Ala Ser Tyr Lys Tyr Ser Glu Glu Ala Asn Asn Leu Ile
        115                 120                 125
Glu Glu Cys Glu Gln Ala Glu Arg Leu Gly Ala Val Asp Glu Ser Leu
    130                 135                 140
Ser Glu Glu Thr Gln Lys Ala Val Leu Gln Trp Thr Lys His Asp Asp
145                 150                 155                 160
Ser Ser Asp Asn Phe Cys Glu Ala Asp Asp Ile Gln Ser Pro Glu Ala
                165                 170                 175
```

```
Glu Tyr Val Asp Leu Leu Leu Asn Pro Glu Arg Tyr Thr Gly Tyr Lys
            180                 185                 190

Gly Pro Asp Ala Trp Lys Ile Trp Asn Val Ile Tyr Glu Glu Asn Cys
        195                 200                 205

Phe Lys Pro Gln Thr Ile Lys Arg Pro Leu Asn Pro Leu Ala Ser Gly
    210                 215                 220

Gln Gly Thr Ser Glu Glu Asn Thr Phe Tyr Ser Trp Leu Glu Gly Leu
225                 230                 235                 240

Cys Val Glu Lys Arg Ala Phe Tyr Arg Leu Ile Ser Gly Leu His Ala
                245                 250                 255

Ser Ile Asn Val His Leu Ser Ala Arg Tyr Leu Leu Gln Glu Thr Trp
            260                 265                 270

Leu Glu Lys Lys Trp Gly His Asn Ile Thr Glu Phe Gln Gln Arg Phe
        275                 280                 285

Asp Gly Ile Leu Thr Glu Gly Glu Gly Pro Arg Arg Leu Lys Asn Leu
    290                 295                 300

Tyr Phe Leu Tyr Leu Ile Glu Leu Arg Ala Leu Ser Lys Val Leu Pro
305                 310                 315                 320

Phe Phe Glu Arg Pro Asp Phe Gln Leu Phe Thr Gly Asn Lys Ile Gln
                325                 330                 335

Asp Glu Glu Asn Lys Met Leu Leu Leu Glu Ile Leu His Glu Ile Lys
            340                 345                 350

Ser Phe Pro Leu His Phe Asp Glu Asn Ser Phe Phe Ala Gly Asp Lys
        355                 360                 365

Lys Glu Ala His Lys Leu Lys Glu Asp Phe Arg Leu His Phe Arg Asn
    370                 375                 380

Ile Ser Arg Ile Met Asp Cys Val Gly Cys Phe Lys Cys Arg Leu Trp
385                 390                 395                 400

Gly Lys Leu Gln Thr Gln Gly Leu Gly Thr Ala Leu Lys Ile Leu Phe
                405                 410                 415

Ser Glu Lys Leu Ile Ala Asn Met Pro Glu Ser Gly Pro Ser Tyr Glu
            420                 425                 430

Phe His Leu Thr Arg Gln Glu Ile Val Ser Leu Phe Asn Ala Phe Gly
        435                 440                 445

Arg Ile Ser Thr Ser Val Lys Glu Leu Glu Asn Phe Arg Asn Leu Leu
    450                 455                 460

Gln Asn Ile His
465

<210> SEQ ID NO 3
<211> LENGTH: 467
<212> TYPE: PRT
<213> ORGANISM: Homo sapiens

<400> SEQUENCE: 3

Met Ser Gln Gly Val Arg Arg Ala Gly Ala Gly Gln Gly Val Ala Ala
1               5                   10                  15

Ala Val Gln Leu Leu Val Thr Leu Ser Phe Leu Arg Ser Val Val Glu
            20                  25                  30

Ala Gln Val Thr Gly Val Leu Asp Asp Cys Leu Cys Asp Ile Asp Ser
        35                  40                  45

Ile Asp Asn Phe Asn Thr Tyr Lys Ile Phe Pro Lys Ile Lys Lys Leu
    50                  55                  60

Gln Glu Arg Asp Tyr Phe Arg Tyr Tyr Lys Val Asn Leu Lys Arg Pro
65                  70                  75                  80
```

-continued

Cys Pro Phe Trp Ala Glu Asp Gly His Cys Ser Ile Lys Asp Cys His
                    85                  90                  95

Val Glu Pro Cys Pro Glu Ser Lys Ile Pro Val Gly Ile Lys Ala Gly
                100                 105                 110

His Ser Asn Lys Tyr Leu Lys Met Ala Asn Asn Thr Lys Glu Leu Glu
            115                 120                 125

Asp Cys Glu Gln Ala Asn Lys Leu Gly Ala Ile Asn Ser Thr Leu Ser
        130                 135                 140

Asn Gln Ser Lys Glu Ala Phe Ile Asp Trp Ala Arg Tyr Asp Asp Ser
145                 150                 155                 160

Arg Asp His Phe Cys Glu Leu Asp Asp Glu Arg Ser Pro Ala Ala Gln
                165                 170                 175

Tyr Val Asp Leu Leu Leu Asn Pro Glu Arg Tyr Thr Gly Tyr Lys Gly
                180                 185                 190

Thr Ser Ala Trp Arg Val Trp Asn Ser Ile Tyr Glu Glu Asn Cys Phe
            195                 200                 205

Lys Pro Arg Ser Val Tyr Arg Pro Leu Asn Pro Leu Ala Pro Ser Arg
        210                 215                 220

Gly Glu Asp Asp Gly Glu Ser Phe Tyr Thr Trp Leu Glu Gly Leu Cys
225                 230                 235                 240

Leu Glu Lys Arg Val Phe Tyr Lys Leu Ile Ser Gly Leu His Ala Ser
                245                 250                 255

Ile Asn Leu His Leu Cys Ala Asn Tyr Leu Leu Glu Glu Thr Trp Gly
                260                 265                 270

Lys Pro Ser Trp Gly Pro Asn Ile Lys Glu Phe Lys His Arg Phe Asp
        275                 280                 285

Pro Val Glu Thr Lys Gly Glu Gly Pro Arg Arg Leu Lys Asn Leu Tyr
        290                 295                 300

Phe Leu Tyr Leu Ile Glu Leu Arg Ala Leu Ser Lys Val Ala Pro Tyr
305                 310                 315                 320

Phe Glu Arg Ser Ile Val Asp Leu Tyr Thr Gly Asn Ala Glu Glu Asp
                325                 330                 335

Ala Asp Thr Lys Thr Leu Leu Leu Asn Ile Phe Gln Thr Lys Ser
                340                 345                 350

Phe Pro Met His Phe Asp Glu Lys Ser Met Phe Ala Gly Asp Lys Lys
            355                 360                 365

Gly Ala Lys Ser Leu Lys Glu Glu Phe Arg Leu His Phe Lys Asn Ile
        370                 375                 380

Ser Arg Ile Met Asp Cys Val Gly Cys Asp Lys Cys Arg Leu Trp Gly
385                 390                 395                 400

Lys Leu Gln Thr Gln Gly Leu Gly Thr Ala Leu Lys Ile Leu Phe Ser
                405                 410                 415

Glu Lys Glu Ile Gln Lys Leu Pro Glu Asn Ser Pro Ser Lys Gly Phe
                420                 425                 430

Gln Leu Thr Arg Gln Glu Ile Val Ala Leu Leu Asn Ala Phe Gly Arg
        435                 440                 445

Leu Ser Thr Ser Ile Arg Asp Leu Gln Asn Phe Lys Val Leu Leu Gln
        450                 455                 460

His Ser Arg
465

<210> SEQ ID NO 4
<211> LENGTH: 205

<212> TYPE: PRT
<213> ORGANISM: Homo sapiens

<400> SEQUENCE: 4

```
Met Ala Ala Pro Gly Glu Arg Gly Arg Phe His Gly Gly Asn Leu Phe
1               5                   10                  15

Phe Leu Pro Gly Gly Ala Arg Ser Glu Met Met Asp Asp Leu Ala Thr
            20                  25                  30

Asp Ala Arg Gly Arg Gly Ala Gly Arg Arg Asp Ala Ala Ala Ser Ala
        35                  40                  45

Ser Thr Pro Ala Gln Ala Pro Thr Ser Asp Ser Pro Val Ala Glu Asp
    50                  55                  60

Ala Ser Arg Arg Arg Pro Cys Arg Ala Cys Val Asp Phe Lys Thr Trp
65                  70                  75                  80

Met Arg Thr Gln Gln Lys Arg Asp Thr Lys Phe Arg Glu Asp Cys Pro
                85                  90                  95

Pro Asp Arg Glu Glu Leu Gly Arg His Ser Trp Ala Val Leu His Thr
            100                 105                 110

Leu Ala Ala Tyr Tyr Pro Asp Leu Pro Thr Pro Glu Gln Gln Gln Asp
        115                 120                 125

Met Ala Gln Phe Ile His Leu Phe Ser Lys Phe Tyr Pro Cys Glu Glu
130                 135                 140

Cys Ala Glu Asp Leu Arg Lys Arg Leu Cys Arg Asn His Pro Asp Thr
145                 150                 155                 160

Arg Thr Arg Ala Cys Phe Thr Gln Trp Leu Cys His Leu His Asn Glu
                165                 170                 175

Val Asn Arg Lys Leu Gly Lys Pro Asp Phe Asp Cys Ser Lys Val Asp
            180                 185                 190

Glu Arg Trp Arg Asp Gly Trp Lys Asp Gly Ser Cys Asp
        195                 200                 205
```

<210> SEQ ID NO 5
<211> LENGTH: 189
<212> TYPE: PRT
<213> ORGANISM: Saccharomyces cerevisiae

<400> SEQUENCE: 5

```
Met Lys Ala Ile Asp Lys Met Thr Asp Asn Pro Pro Gln Glu Gly Leu
1               5                   10                  15

Ser Gly Arg Lys Ile Ile Tyr Asp Glu Asp Gly Lys Pro Cys Arg Ser
            20                  25                  30

Cys Asn Thr Leu Leu Asp Phe Gln Tyr Val Thr Gly Lys Ile Ser Asn
        35                  40                  45

Gly Leu Lys Asn Leu Ser Ser Asn Gly Lys Leu Ala Gly Thr Gly Ala
    50                  55                  60

Leu Thr Gly Glu Ala Ser Glu Leu Met Pro Gly Ser Arg Thr Tyr Arg
65                  70                  75                  80

Lys Val Asp Pro Pro Asp Val Glu Gln Leu Gly Arg Ser Ser Trp Thr
                85                  90                  95

Leu Leu His Ser Val Ala Ala Ser Tyr Pro Ala Gln Pro Thr Asp Gln
            100                 105                 110

Gln Lys Gly Glu Met Lys Gln Phe Leu Asn Ile Phe Ser His Ile Tyr
        115                 120                 125

Pro Cys Asn Trp Cys Ala Lys Asp Phe Glu Lys Tyr Ile Arg Glu Asn
    130                 135                 140
```

```
Ala Pro Gln Val Glu Ser Arg Glu Leu Gly Arg Trp Met Cys Glu
145                 150                 155                 160

Ala His Asn Lys Val Asn Lys Lys Leu Arg Lys Pro Lys Phe Asp Cys
                165                 170                 175

Asn Phe Trp Glu Lys Arg Trp Lys Asp Gly Trp Asp Glu
            180                 185

<210> SEQ ID NO 6
<211> LENGTH: 196
<212> TYPE: PRT
<213> ORGANISM: Saccharomyces cerevisiae

<400> SEQUENCE: 6

Met Lys Gln Ile Val Lys Arg Ser His Ala Ile Arg Ile Val Ala Ala
1               5                   10                  15

Leu Gly Ile Ile Gly Leu Trp Met Phe Phe Ser Ser Asn Glu Leu Ser
                20                  25                  30

Ile Ala Thr Pro Gly Leu Ile Lys Ala Lys Ser Gly Ile Asp Glu Val
            35                  40                  45

Gln Gly Ala Ala Ala Glu Lys Asn Asp Ala Arg Leu Lys Glu Ile Glu
    50                  55                  60

Lys Gln Thr Ile Met Pro Leu Met Gly Asp Asp Lys Val Lys Lys Glu
65                  70                  75                  80

Val Gly Arg Ala Ser Trp Lys Tyr Phe His Thr Leu Leu Ala Arg Phe
                85                  90                  95

Pro Asp Glu Pro Thr Pro Glu Glu Arg Glu Lys Leu His Thr Phe Ile
            100                 105                 110

Gly Leu Tyr Ala Glu Leu Tyr Pro Cys Gly Glu Cys Ser Tyr His Phe
        115                 120                 125

Val Lys Leu Ile Glu Lys Tyr Pro Val Gln Thr Ser Ser Arg Thr Ala
    130                 135                 140

Ala Ala Met Trp Gly Cys His Ile His Asn Lys Val Asn Glu Tyr Leu
145                 150                 155                 160

Lys Lys Asp Ile Tyr Asp Cys Ala Thr Ile Leu Glu Asp Tyr Asp Cys
                165                 170                 175

Gly Cys Ser Asp Ser Asp Gly Lys Arg Val Ser Leu Glu Lys Glu Ala
            180                 185                 190

Lys Gln His Gly
        195

<210> SEQ ID NO 7
<211> LENGTH: 747
<212> TYPE: PRT
<213> ORGANISM: Homo sapiens

<400> SEQUENCE: 7

Met Arg Arg Cys Asn Ser Gly Ser Gly Pro Pro Pro Ser Leu Leu Leu
1               5                   10                  15

Leu Leu Leu Trp Leu Leu Ala Val Pro Gly Ala Asn Ala Ala Pro Arg
                20                  25                  30

Ser Ala Leu Tyr Ser Pro Ser Asp Pro Leu Thr Leu Leu Gln Ala Asp
            35                  40                  45

Thr Val Arg Gly Ala Val Leu Gly Ser Arg Ser Ala Trp Ala Val Glu
    50                  55                  60

Phe Phe Ala Ser Trp Cys Gly His Cys Ile Ala Phe Ala Pro Thr Trp
65                  70                  75                  80
```

-continued

Lys Ala Leu Ala Glu Asp Val Lys Ala Trp Arg Pro Ala Leu Tyr Leu
            85                  90                  95

Ala Ala Leu Asp Cys Ala Glu Glu Thr Asn Ser Ala Val Cys Arg Asp
            100                 105                 110

Phe Asn Ile Pro Gly Phe Pro Thr Val Arg Phe Phe Lys Ala Phe Thr
            115                 120                 125

Lys Asn Gly Ser Gly Ala Val Phe Pro Val Ala Gly Ala Asp Val Gln
            130                 135                 140

Thr Leu Arg Glu Arg Leu Ile Asp Ala Leu Glu Ser His His Asp Thr
145                 150                 155                 160

Trp Pro Pro Ala Cys Pro Pro Leu Glu Pro Ala Lys Leu Glu Glu Ile
            165                 170                 175

Asp Gly Phe Phe Ala Arg Asn Asn Glu Glu Tyr Leu Ala Leu Ile Phe
            180                 185                 190

Glu Lys Gly Gly Ser Tyr Leu Gly Arg Glu Val Ala Leu Asp Leu Ser
            195                 200                 205

Gln His Lys Gly Val Ala Val Arg Arg Val Leu Asn Thr Glu Ala Asn
            210                 215                 220

Val Val Arg Lys Phe Gly Val Thr Asp Phe Pro Ser Cys Tyr Leu Leu
225                 230                 235                 240

Phe Arg Asn Gly Ser Val Ser Arg Val Pro Val Leu Met Glu Ser Arg
            245                 250                 255

Ser Phe Tyr Thr Ala Tyr Leu Gln Arg Leu Ser Gly Leu Thr Arg Glu
            260                 265                 270

Ala Ala Gln Thr Thr Val Ala Pro Thr Thr Ala Asn Lys Ile Ala Pro
            275                 280                 285

Thr Val Trp Lys Leu Ala Asp Arg Ser Lys Ile Tyr Met Ala Asp Leu
            290                 295                 300

Glu Ser Ala Leu His Tyr Ile Leu Arg Ile Glu Val Gly Arg Phe Pro
305                 310                 315                 320

Val Leu Glu Gly Gln Arg Leu Val Ala Leu Lys Lys Phe Val Ala Val
            325                 330                 335

Leu Ala Lys Tyr Phe Pro Gly Arg Pro Leu Val Gln Asn Phe Leu His
            340                 345                 350

Ser Val Asn Glu Trp Leu Lys Arg Gln Lys Arg Asn Lys Ile Pro Tyr
            355                 360                 365

Ser Phe Phe Lys Thr Ala Leu Asp Asp Arg Lys Glu Gly Ala Val Leu
            370                 375                 380

Ala Lys Lys Val Asn Trp Ile Gly Cys Gln Gly Ser Glu Pro His Phe
385                 390                 395                 400

Arg Gly Phe Pro Cys Ser Leu Trp Val Leu Phe His Phe Leu Thr Val
            405                 410                 415

Gln Ala Ala Arg Gln Asn Val Asp His Ser Gln Glu Ala Ala Lys Ala
            420                 425                 430

Lys Glu Val Leu Pro Ala Ile Arg Gly Tyr Val His Tyr Phe Phe Gly
            435                 440                 445

Cys Arg Asp Cys Ala Ser His Phe Glu Gln Met Ala Ala Ala Ser Met
            450                 455                 460

His Arg Val Gly Ser Pro Asn Ala Ala Val Leu Trp Leu Trp Ser Ser
465                 470                 475                 480

His Asn Arg Val Asn Ala Arg Leu Ala Gly Ala Pro Ser Glu Asp Pro
            485                 490                 495

Gln Phe Pro Lys Val Gln Trp Pro Pro Arg Glu Leu Cys Ser Ala Cys

```
                    500                 505                 510
        His Asn Glu Arg Leu Asp Val Pro Val Trp Asp Val Glu Ala Thr Leu
                        515                 520                 525

Asn Phe Leu Lys Ala His Phe Ser Pro Ser Asn Ile Ile Leu Asp Phe
                    530                 535                 540

Pro Ala Ala Gly Ser Ala Ala Arg Arg Asp Val Gln Asn Val Ala Ala
        545                 550                 555                 560

Ala Pro Glu Leu Ala Met Gly Ala Leu Glu Leu Glu Ser Arg Asn Ser
                        565                 570                 575

Thr Leu Asp Pro Gly Lys Pro Glu Met Met Lys Ser Pro Thr Asn Thr
                    580                 585                 590

Thr Pro His Val Pro Ala Glu Gly Pro Glu Ala Ser Arg Pro Pro Lys
                        595                 600                 605

Leu His Pro Gly Leu Arg Ala Ala Pro Gly Gln Glu Pro Pro Glu His
                    610                 615                 620

Met Ala Glu Leu Gln Arg Asn Glu Gln Glu Gln Pro Leu Gly Gln Trp
        625                 630                 635                 640

His Leu Ser Lys Arg Asp Thr Gly Ala Ala Leu Leu Ala Glu Ser Arg
                        645                 650                 655

Ala Glu Lys Asn Arg Leu Trp Gly Pro Leu Glu Val Arg Arg Val Gly
                    660                 665                 670

Arg Ser Ser Lys Gln Leu Val Asp Ile Pro Glu Gly Gln Leu Glu Ala
                        675                 680                 685

Arg Ala Gly Arg Gly Arg Gly Gln Trp Leu Val Leu Gly Gly Gly
                    690                 695                 700

Phe Ser Tyr Leu Asp Ile Ser Leu Cys Val Gly Leu Tyr Ser Leu Ser
        705                 710                 715                 720

Phe Met Gly Leu Leu Ala Met Tyr Thr Tyr Phe Gln Ala Lys Ile Arg
                        725                 730                 735

Ala Leu Lys Gly His Ala Gly His Pro Ala Ala
                    740                 745

<210> SEQ ID NO 8
<211> LENGTH: 698
<212> TYPE: PRT
<213> ORGANISM: Homo sapiens

<400> SEQUENCE: 8

Met Ala Ala Ala Gly Ala Ala Val Ala Arg Ser Pro Gly Ile Gly Ala
        1               5                   10                  15

Gly Pro Ala Leu Arg Ala Arg Arg Ser Pro Pro Arg Ala Ala Arg
                        20                  25                  30

Leu Pro Arg Leu Leu Val Leu Leu Ala Ala Ala Val Gly Pro Gly
                    35                  40                  45

Ala Gly Gly Ala Ala Arg Leu Tyr Arg Ala Gly Glu Asp Ala Val Trp
        50                  55                  60

Val Leu Asp Ser Gly Ser Val Arg Gly Ala Thr Ala Asn Ser Ser Ala
        65                  70                  75                  80

Ala Trp Leu Val Gln Phe Tyr Ser Ser Trp Cys Gly His Cys Ile Gly
                        85                  90                  95

Tyr Ala Pro Thr Trp Arg Ala Leu Ala Gly Asp Val Arg Asp Trp Ala
                    100                 105                 110

Ser Ala Ile Arg Val Ala Ala Leu Asp Cys Met Glu Glu Lys Asn Gln
                    115                 120                 125
```

```
Ala Val Cys His Asp Tyr Asp Ile His Phe Tyr Pro Thr Phe Arg Tyr
130                 135                 140

Phe Lys Ala Phe Thr Lys Glu Phe Thr Thr Gly Glu Asn Phe Lys Gly
145                 150                 155                 160

Pro Asp Arg Glu Leu Arg Thr Val Arg Gln Thr Met Ile Asp Phe Leu
                165                 170                 175

Gln Asn His Thr Glu Gly Ser Arg Pro Pro Ala Cys Pro Arg Leu Asp
            180                 185                 190

Pro Ile Gln Pro Ser Asp Val Leu Ser Leu Leu Asp Asn Arg Gly Ser
        195                 200                 205

His Tyr Val Ala Ile Val Phe Glu Ser Asn Ser Ser Tyr Leu Gly Arg
    210                 215                 220

Glu Val Ile Leu Asp Leu Ile Pro Tyr Glu Ser Ile Val Val Thr Arg
225                 230                 235                 240

Ala Leu Asp Gly Asp Lys Ala Phe Leu Glu Lys Leu Gly Val Ser Ser
                245                 250                 255

Val Pro Ser Cys Tyr Leu Ile Tyr Pro Asn Gly Ser His Gly Leu Ile
            260                 265                 270

Asn Val Val Lys Pro Leu Arg Ala Phe Phe Ser Ser Tyr Leu Lys Ser
        275                 280                 285

Leu Pro Asp Val Arg Lys Lys Ser Leu Pro Leu Pro Glu Lys Pro His
    290                 295                 300

Lys Glu Glu Asn Ser Glu Ile Val Val Trp Arg Glu Phe Asp Lys Ser
305                 310                 315                 320

Lys Leu Tyr Thr Val Asp Leu Glu Ser Gly Leu His Tyr Leu Leu Arg
                325                 330                 335

Val Glu Leu Ala Ala His Lys Ser Leu Ala Gly Ala Glu Leu Lys Thr
            340                 345                 350

Leu Lys Asp Phe Val Thr Val Leu Ala Lys Leu Phe Pro Gly Arg Pro
        355                 360                 365

Pro Val Lys Lys Leu Leu Glu Met Leu Gln Glu Trp Leu Ala Ser Leu
    370                 375                 380

Pro Leu Asp Arg Ile Pro Tyr Asn Ala Val Leu Asp Leu Val Asn Asn
385                 390                 395                 400

Lys Met Arg Ile Ser Gly Ile Phe Leu Thr Asn His Ile Lys Trp Val
                405                 410                 415

Gly Cys Gln Gly Ser Arg Ser Glu Leu Arg Gly Tyr Pro Cys Ser Leu
            420                 425                 430

Trp Lys Leu Phe His Thr Leu Thr Val Glu Ala Ser Thr His Pro Asp
        435                 440                 445

Ala Leu Val Gly Thr Gly Phe Glu Asp Asp Pro Gln Ala Val Leu Gln
    450                 455                 460

Thr Met Arg Arg Tyr Val His Thr Phe Phe Gly Cys Lys Glu Cys Gly
465                 470                 475                 480

Glu His Phe Glu Glu Met Ala Lys Glu Ser Met Asp Ser Val Lys Thr
                485                 490                 495

Pro Asp Gln Ala Ile Leu Trp Leu Trp Lys Lys His Asn Met Val Asn
            500                 505                 510

Gly Arg Leu Ala Gly His Leu Ser Glu Asp Pro Arg Phe Pro Lys Leu
        515                 520                 525

Gln Trp Pro Thr Pro Asp Leu Cys Pro Ala Cys His Glu Glu Ile Lys
    530                 535                 540

Gly Leu Ala Ser Trp Asp Glu Gly His Val Leu Thr Phe Leu Lys Gln
```

```
                545                 550                 555                 560
        His Tyr Gly Arg Asp Asn Leu Leu Asp Thr Tyr Ser Ala Asp Gln Gly
                        565                 570                 575

Asp Ser Ser Glu Gly Gly Thr Leu Ala Arg Gly Glu Glu Glu Lys
                580                 585                 590

Arg Leu Thr Pro Pro Glu Val Ser His Gly Asp Arg Asp Thr Gln Ser
                        595                 600                 605

Val Arg Pro Pro Gly Ala Leu Gly Pro Arg Pro Ala Leu Pro Glu Ser
                610                 615                 620

Leu His His Ser Leu Asp Gly Lys Leu Gln Ser Leu Asp Gly Pro Gly
        625                 630                 635                 640

Ala His Lys Glu Val Gly Gly Ala Ala Pro Phe Leu Gly Val Asp Phe
                        645                 650                 655

Ser Ser Leu Asp Met Ser Leu Cys Val Val Leu Tyr Val Ala Ser Ser
                        660                 665                 670

Leu Phe Leu Met Val Met Tyr Phe Phe Phe Arg Val Arg Ser Arg Arg
                        675                 680                 685

Trp Lys Val Lys His His His Pro Ala Val
                690                 695

<210> SEQ ID NO 9
<211> LENGTH: 95
<212> TYPE: PRT
<213> ORGANISM: Vaccinia virus

<400> SEQUENCE: 9

Met Asn Pro Lys His Trp Gly Arg Ala Val Trp Thr Ile Ile Phe Ile
        1               5                   10                  15

Val Leu Ser Gln Ala Gly Leu Asp Gly Asn Ile Glu Ala Cys Lys Arg
                        20                  25                  30

Lys Leu Tyr Thr Ile Val Ser Thr Leu Pro Cys Pro Ala Cys Arg Arg
                    35                  40                  45

His Ala Thr Ile Ala Ile Glu Asp Asn Val Met Ser Ser Asp Asp
            50                  55                  60

Leu Asn Tyr Ile Tyr Tyr Phe Phe Ile Arg Leu Phe Asn Asn Leu Ala
        65                  70                  75                  80

Ser Asp Pro Lys Tyr Ala Ile Asp Val Ser Lys Val Lys Pro Leu
                        85                  90                  95

<210> SEQ ID NO 10
<211> LENGTH: 236
<212> TYPE: PRT
<213> ORGANISM: Escherichia coli

<400> SEQUENCE: 10

Met Lys Lys Gly Phe Met Leu Phe Thr Leu Leu Ala Ala Phe Ser Gly
        1               5                   10                  15

Phe Ala Gln Ala Asp Asp Ala Ala Ile Gln Gln Thr Leu Ala Lys Met
                        20                  25                  30

Gly Ile Lys Ser Ser Asp Ile Gln Pro Ala Pro Val Ala Gly Met Lys
                    35                  40                  45

Thr Val Leu Thr Asn Ser Gly Val Leu Tyr Ile Thr Asp Asp Gly Lys
                50                  55                  60

His Ile Ile Gln Gly Pro Met Tyr Asp Val Ser Gly Thr Ala Pro Val
        65                  70                  75                  80

Asn Val Thr Asn Lys Met Leu Leu Lys Gln Leu Asn Ala Leu Glu Lys
```

```
                        85                  90                  95
Glu Met Ile Val Tyr Lys Ala Pro Gln Glu Lys His Val Ile Thr Val
                100                 105                 110
Phe Thr Asp Ile Thr Cys Gly Tyr Cys His Lys Leu His Glu Gln Met
            115                 120                 125
Ala Asp Tyr Asn Ala Leu Gly Ile Thr Val Arg Tyr Leu Ala Phe Pro
        130                 135                 140
Arg Gln Gly Leu Asp Ser Asp Ala Glu Lys Glu Met Lys Ala Ile Trp
145                 150                 155                 160
Cys Ala Lys Asp Lys Asn Lys Ala Phe Asp Asp Val Met Ala Gly Lys
                165                 170                 175
Ser Val Ala Pro Ala Ser Cys Asp Val Asp Ile Ala Asp His Tyr Ala
                180                 185                 190
Leu Gly Val Gln Leu Gly Val Ser Gly Thr Pro Ala Val Val Leu Ser
            195                 200                 205
Asn Gly Thr Leu Val Pro Gly Tyr Gln Pro Pro Lys Glu Met Lys Glu
        210                 215                 220
Phe Leu Asp Glu His Gln Lys Met Thr Ser Gly Lys
225                 230                 235

<210> SEQ ID NO 11
<211> LENGTH: 508
<212> TYPE: PRT
<213> ORGANISM: Homo sapiens

<400> SEQUENCE: 11

Met Leu Arg Arg Ala Leu Leu Cys Leu Ala Val Ala Ala Leu Val Arg
1               5                   10                  15
Ala Asp Ala Pro Glu Glu Glu Asp His Val Leu Val Leu Arg Lys Ser
                20                  25                  30
Asn Phe Ala Glu Ala Leu Ala Ala His Lys Tyr Leu Leu Val Glu Phe
            35                  40                  45
Tyr Ala Pro Trp Cys Gly His Cys Lys Ala Leu Ala Pro Glu Tyr Ala
        50                  55                  60
Lys Ala Ala Gly Lys Leu Lys Ala Glu Gly Ser Glu Ile Arg Leu Ala
65                  70                  75                  80
Lys Val Asp Ala Thr Glu Glu Ser Asp Leu Ala Gln Gln Tyr Gly Val
                85                  90                  95
Arg Gly Tyr Pro Thr Ile Lys Phe Phe Arg Asn Gly Asp Thr Ala Ser
                100                 105                 110
Pro Lys Glu Tyr Thr Ala Gly Arg Glu Ala Asp Asp Ile Val Asn Trp
            115                 120                 125
Leu Lys Lys Arg Thr Gly Pro Ala Ala Thr Thr Leu Pro Asp Gly Ala
        130                 135                 140
Ala Ala Glu Ser Leu Val Glu Ser Ser Glu Val Ala Val Ile Gly Phe
145                 150                 155                 160
Phe Lys Asp Val Glu Ser Asp Ser Ala Lys Gln Phe Leu Gln Ala Ala
                165                 170                 175
Glu Ala Ile Asp Asp Ile Pro Phe Gly Ile Thr Ser Asn Ser Asp Val
                180                 185                 190
Phe Ser Lys Tyr Gln Leu Asp Lys Asp Gly Val Val Leu Phe Lys Lys
            195                 200                 205
Phe Asp Glu Gly Arg Asn Asn Phe Glu Gly Glu Val Thr Lys Glu Asn
        210                 215                 220
```

```
Leu Leu Asp Phe Ile Lys His Asn Gln Leu Pro Leu Val Ile Glu Phe
225                 230                 235                 240

Thr Glu Gln Thr Ala Pro Lys Ile Phe Gly Gly Glu Ile Lys Thr His
            245                 250                 255

Ile Leu Leu Phe Leu Pro Lys Ser Val Ser Asp Tyr Asp Gly Lys Leu
        260                 265                 270

Ser Asn Phe Lys Thr Ala Ala Glu Ser Phe Lys Gly Lys Ile Leu Phe
    275                 280                 285

Ile Phe Ile Asp Ser Asp His Thr Asp Asn Gln Arg Ile Leu Glu Phe
290                 295                 300

Phe Gly Leu Lys Lys Glu Glu Cys Pro Ala Val Arg Leu Ile Thr Leu
305                 310                 315                 320

Glu Glu Glu Met Thr Lys Tyr Lys Pro Glu Ser Glu Glu Leu Thr Ala
            325                 330                 335

Glu Arg Ile Thr Glu Phe Cys His Arg Phe Leu Glu Gly Lys Ile Lys
            340                 345                 350

Pro His Leu Met Ser Gln Glu Leu Pro Glu Asp Trp Asp Lys Gln Pro
        355                 360                 365

Val Lys Val Leu Val Gly Lys Asn Phe Glu Asp Val Ala Phe Asp Glu
370                 375                 380

Lys Lys Asn Val Phe Val Glu Phe Tyr Ala Pro Trp Cys Gly His Cys
385                 390                 395                 400

Lys Gln Leu Ala Pro Ile Trp Asp Lys Leu Gly Glu Thr Tyr Lys Asp
                405                 410                 415

His Glu Asn Ile Val Ile Ala Lys Met Asp Ser Thr Ala Asn Glu Val
            420                 425                 430

Glu Ala Val Lys Val His Ser Phe Pro Thr Leu Lys Phe Phe Pro Ala
            435                 440                 445

Ser Ala Asp Arg Thr Val Ile Asp Tyr Asn Gly Glu Arg Thr Leu Asp
    450                 455                 460

Gly Phe Lys Lys Phe Leu Glu Ser Gly Gly Gln Asp Gly Ala Gly Asp
465                 470                 475                 480

Asp Asp Asp Leu Glu Asp Leu Glu Glu Ala Glu Glu Pro Asp Met Glu
                485                 490                 495

Glu Asp Asp Asp Gln Lys Ala Val Lys Asp Glu Leu
                500                 505

<210> SEQ ID NO 12
<211> LENGTH: 8
<212> TYPE: PRT
<213> ORGANISM: Artificial sequence
<220> FEATURE:
<223> OTHER INFORMATION: chemically synthesized

<400> SEQUENCE: 12

Met His His His His His His Met
1               5

<210> SEQ ID NO 13
<211> LENGTH: 10
<212> TYPE: PRT
<213> ORGANISM: Artificial sequence
<220> FEATURE:
<223> OTHER INFORMATION: Chemically synthesized

<400> SEQUENCE: 13

Asn Ser Ser Ser Asn Asn Asn Asn His Met
1               5                   10
```

```
<210> SEQ ID NO 14
<211> LENGTH: 26
<212> TYPE: PRT
<213> ORGANISM: Artificial sequence
<220> FEATURE:
<223> OTHER INFORMATION: chemically synthesized

<400> SEQUENCE: 14

Gly Ser Gly Ser Gly Ser Gly Ser Gly Ser Ile Glu Gly Arg Gly Ser
1               5                   10                  15

Gly Ser Gly Ser Gly Ser Gly Ser His Met
            20                  25
```